(12) United States Patent
Hamada et al.

(10) Patent No.: US 7,704,224 B2
(45) Date of Patent: Apr. 27, 2010

(54) METHOD FOR TESTING PERITONEUM FUNCTION AND A PERITONEAL DIALYSIS PLANNING APPARATUS

(75) Inventors: Hiroyuki Hamada, Fukuoka (JP); Masahiro Okamoto, Iizuka (JP)

(73) Assignee: JMS Co., Ltd., Hiroshima (JP)

( * ) Notice: Subject to any disclaimer, the term of this patent is extended or adjusted under 35 U.S.C. 154(b) by 1048 days.

(21) Appl. No.: 10/556,394

(22) PCT Filed: May 13, 2004

(86) PCT No.: PCT/JP2004/006774

§ 371 (c)(1),
(2), (4) Date: Nov. 10, 2005

(87) PCT Pub. No.: WO2004/101032

PCT Pub. Date: Nov. 25, 2004

(65) Prior Publication Data

US 2006/0287585 A1      Dec. 21, 2006

(30) Foreign Application Priority Data

May 14, 2003 (JP) ............................. 2003-136066
Apr. 15, 2004 (JP) ............................. 2004-120705

(51) Int. Cl.
*A61M 1/00*      (2006.01)
(52) U.S. Cl. ................. 604/29; 210/646; 210/647; 700/271; 424/520
(58) Field of Classification Search .............. 604/29; 210/646–647; 700/271; 424/520
See application file for complete search history.

(56) References Cited

U.S. PATENT DOCUMENTS 5,670,057 A     9/1997  Chen et al.
2002/0075227 A1*  6/2002  Miller et al. ............. 345/156

FOREIGN PATENT DOCUMENTS

| JP | 10-502569 | 3/1998 |
| JP | 2000-140100 | 5/2000 |
| JP | 3661980 | 4/2005 |
| WO | 96/33753 | 10/1996 |

OTHER PUBLICATIONS

Akiyasu Yamashita, "Peritoneal function and its evaluation", Kidney and Dialysis, Jun. 2002, vol. 52, No. 6, pp. 705-708.

* cited by examiner

*Primary Examiner*—Tony G Soohoo
*Assistant Examiner*—Robert Eom
(74) *Attorney, Agent, or Firm*—Wenderoth, Lind & Ponack, L.L.P.

(57) ABSTRACT

A peritoneal function testing method of using a ratio $MTAC_{un}/MTAC_c$ calculated using $MTAC_{un}$ and $MTAC_c$ as an index for a peritoneal function test. $MTAC_{un}$ is an overall mass transfer-area coefficient for urea nitrogen and $MTAC_c$ is an overall mass transfer-area coefficient for creatinine. Use of the $MTAC_{un}/MTAC_c$ ratio enables examination of the future peritoneal function of a patient (a mechanism of deterioration in peritoneal function). $MTAC_{un}$ and $MTAC_c$ are obtained using a Pyle-Popovich model. The peritoneal function testing method further calculates a permeability coefficient for cell pores ($L_PS_C$) and an overall permeability coefficient ($L_PS$) from a Three-Pore Theory model to obtain a ratio $L_PS_C/L_PS$ calculated using the $L_PS_C$ and the $L_PS$, and further uses the $L_PS_C/L_PS$ ratio and the $MTAC_{un}/MTAC_c$ ratio as indexes for the peritoneal function test.

12 Claims, 16 Drawing Sheets

MASS TRANSFER MECHANISM IN PERITONEAL DIALYSIS

MASS TRANSFER PHENOMENON ACROSS A PERITONEUM,
BASED ON THREE-PORE THEORY (YAMASHITA, 1998, PARTIALLY MODIFIED)

FIG. 6

PERITONEAL FUNCTION TEST    INPUT DATA ITEMS

| DATE (YY/MM/DD) | YEAR | MONTH | DAY | ~ | MONTH | DAY |
|---|---|---|---|---|---|---|
| FAMILY NAME /GIVEN NAME | | | SEX | M/F | CHART NO. | |
| BIRTH DATE | YEAR | MONTH | DAY | HEIGHT (cm) | | WEIGHT (kg)* |

\*: MEASURED WITH AN EMPTY PERITONEAL CAVITY

| URINE VOLUME (mL) | | URINARY UREA NITROGEN (mg/dL) | | URINARY CREATININE (mg/dL) | |
|---|---|---|---|---|---|
| URINARY PROTEIN (mg/dL) | | URINARY SODIUM (mEq/L) | | | |

| BLOOD SAMPLE 1 (AM 8:00) | | BLOOD SAMPLE 2 (PET-2) | | BLOOD SAMPLE 3 (AM 8:00) | |
|---|---|---|---|---|---|
| TOTAL PROTEIN (g/dL) | | TOTAL PROTEIN (g/dL) | | TOTAL PROTEIN (g/dL) | |
| ALBUMIN (g/dL) | | ALBUMIN (g/dL) | | ALBUMIN (g/dL) | |
| SERUM CREATININE (mg/dL) | | SERUM CREATININE (mg/dL) | | SERUM CREATININE (mg/dL) | |
| UREA NITROGEN (mg/dL) | | UREA NITROGEN (mg/dL) | | UREA NITROGEN (mg/dL) | |
| GLUCOSE (mg/dL) | | GLUCOSE (mg/dL) | | GLUCOSE (mg/dL) | |
| SODIUM (mEq/L) | | SODIUM (mEq/L) | | SODIUM (mEq/L) | |
| CHLORIDE (mEq/L) | | CHLORIDE (mEq/L) | | CHLORIDE (mEq/L) | |

| SYSTEM | PERISATE | TW · ST | | CIRCUIT WEIGHT | g |
|---|---|---|---|---|---|

FIG. 7

| BAG EXCHANGE | SUGAR CONCENTRATION IN MEDICAL SOLUTION | TOTAL WEIGHT OF MEDICAL SOLUTION | START TIME OF DRAINAGE | WEIGHT AFTER DRAINAGE | WEIGHT AFTER PRIMING | FINISH TIME OF INJECTION |
|---|---|---|---|---|---|---|
| | g/dL | g | hr:min | g | g | hr:min |
| 22:30 | | | : | | | : |
| 8:00 | | | : | | | : |
| PET-0 | | | ( : ) | — | — | : |
| PET-2 | — | — | ( : ) | — | — | — |
| PET-4 | — | — | ( : ) | | | : |
| 15:30 | | | : | | | : |
| 20:30 | | | : | | | : |
| 22:30 | | | : | | | : |
| 8:00 | — | — | : | — | — | — |

| TEST OF DRAINED FLUID | PROTEIN CONCENTRATION | ALBUMIN | CREATININE | UREA NITROGEN | GLUCOSE | SODIUM | CHLORIDE |
|---|---|---|---|---|---|---|---|
| | mg/dL | mg/dL | mg/dL | mg/dL | mg/dL | mEq/L | mEq/L |
| — | — | — | — | — | — | — | — |
| $D_1$ | | | | | | | |
| $D_2$ (PET0) | | | | | | | |
| $D_3$ (PET2) | | | | | | | |
| $D_4$ (PET4) | | | | | | | |
| $D_5$ | | | | | | | |
| $D_6$ | | | | | | | |
| $D_7$ | | | | | | | |
| $D_8$ | | | | | | | |

FIG. 16

| ITEM | FIRST EMBODIMENT | SECOND EMBODIMENT |
|---|---|---|
| DIALYSIS SOLUTION EXCHANGES | 6 TIMES | 4 TIMES |
| BLOOD COLLECTIONS | 3 TIMES | ONCE |
| DRAINED FLUID SAMPLES | 8 SAMPLES | 6 SAMPLES |
| BLOOD COLLETION SAMPLES | 3 X 2 SAMPLES | 1 X 2 SAMPLES |
| MEASUREMENT OF VOLUME OF DRAINED FLUID | 6 BAGS | 4 BAGS |
| URINE COLLECTIONS (24hr) | ONCE | ONCE |
| URINE COLLECTION SAMPLES | 1 SAMPLE | 1 SAMPLE |

METHOD FOR TESTING PERITONEUM FUNCTION AND A PERITONEAL DIALYSIS PLANNING APPARATUS

BACKGROUND OF THE INVENTION

1. Field of Invention

The present invention relates to a method for testing peritoneal function and a peritoneal dialysis planning apparatus using a computer.

2. Description of the Related Art

It is believed that there are presently about 200,000 patients with chronic renal failure in Japan. Of them, 92% to 93% receive hemodialysis as a maintenance treatment while the remaining 7% to 8% receive peritoneal dialysis.

"Dialysis" here means a process of removal of certain molecules from body fluid due to a concentration gradient by filtering it across a membrane, making use of different molecular weights. Thus, this process assists impaired renal function of the patients by dissolving various substances, which are accumulated in the body through metabolic activities—solutes (such as urea (U) as a uremic toxin and creatinine (Cr)), electrolytes ($Ca^{2+}$, $Cl^-$, $Na^+$, and $K^+$, excess water and the like, out of the body fluid into a dialysis solution, and by then discharging the dialysis solution from the body as drained fluid. Two distinguished methods used for dialysis are hemodialysis (HD) and peritoneal dialysis (PD). Hemodialysis is a mechanical blood purification procedure to pass blood through the extracorporeal circulation, while peritoneal dialysis is a blood purification procedure achieved by infusing a dialysis solution into the peritoneal cavity and filtering blood through the peritoneum. Conventionally, either of the dialysis procedures can be applied to the patients. In the case when deficient renal function cannot be fully compensated, it is considered as desirable to perform extracorporeal dialysis treatment using hemodialysis.

With peritoneal dialysis, the patients perform dialysis treatment mainly at home. The home dialysis involves the repetition of the following steps several times a day: introduction of a dialysis solution into the peritoneal cavity performed by patients themselves using a catheter; retention of the introduced dialysis solution for several hours; and then drainage of the dialysis solution. The patient records the amount of excess water drained from the body (referred to as the "volume of water removal") every time a dialysis solution is drained, and submits the records to doctors in a subsequent medical examination to obtain a prescription. Such a peritoneal dialysis procedure is called CAPD (Continuous Ambulatory Peritoneal Dialysis). Doctors take particular note of the volume of water removal of the patients, and choose appropriate prescriptions for the patients based on the volume of the drained water.

A peritoneal dialysis system, in which a condition of patient's peritoneal function is simulated by a computer, has been developed in recent years (see Japanese Laid-Open Patent Application Publication No. 2000-140100). This peritoneal dialysis system enables testing aspects of peritoneal function, such as the rates of solute removal and transperitoneal water removal, by computing Pyle-Popovich's mathematical model, known as a macroscopic model of peritoneal dialysis, from patient's data—the concentration of each solute, the volume of water removal and so on included—obtained by using PET (Peritoneal Equilibration Test, 1987). In general, a commercially available personal computer is typically employed in an apparatus operating such a system.

The above-mentioned peritoneal dialysis system is, however, generally capable of only making a diagnosis either qualitatively or quantitatively, although it can assess peritoneal function of a patient at the time when data is collected, based on the concentration of each solute and the volume of water removal. Accordingly, it is very difficult to study future changes in patient's peritoneal function (so-called "a mechanism of deterioration in peritoneal permeability") by using such a system.

For example, as to data obtained from a patient, in the case when an apparent volume of water removal indicated by a numerical value of the data is low, the following can be considered as possible causes. However, it is impossible to determine which of the following is/are the actual cause.

A: water is not drained out since the catheter tip inserted into the peritoneum is physically blocked or malpositioned (external factor);

B: the lymphatic system of the peritoneum has an elevated level of reabsorption capability; and C: actual peritoneal function (the rate of transperitoneal water removal) has been reduced.

Of them, when A is the real cause, the blockage in the catheter is removed or the position is corrected, while anti-inflammatory agents are administered into the lymphatic system when B is the cause. If the cause is C, dialysis modality is switched from peritoneal dialysis to hemodialysis. Thus, the ways of handling the situation are much different depending on the real cause. In addition, when both B and C are the cause, the patient may possibly have complications with peritonitis or encapsulated peritoneal sclerosis, and therefore much consideration has to be given to how to treat the patient. Thus, conventional methods of testing peritoneal function do not fully allow critical judgments to be made to determine appropriate treatments for patients, and therefore, there is still room for improvement.

The present invention has been made in view of the above problems, and aims at offering a method for testing peritoneal function and a peritoneal dialysis planning apparatus which allow (i) an accurate analysis of a peritoneal function (a mechanism of deterioration in peritoneal permeability) of patients with peritoneal dialysis by using various types of data obtained through conventional methods and (ii) the application of the results of the analysis to future diagnostic prescriptions.

BRIEF SUMMARY OF THE INVENTION

In order to solve the above problems, the present invention uses a ratio $MTAC_{un}/MTAC_c$ calculated using $MTAC_{un}$ and $MTAC_c$ as an index for a peritoneal function test, where $MTAC_{un}$ is an overall mass transfer—area coefficient for urea nitrogen and $MTAC_c$ is an overall mass transfer—area coefficient for creatinine.

"$MTAC_{un/c}$" denoted hereinafter means "$MTAC_{un}/MTAC_c$". For convenience of explanation, these notations are separately used depending on the situations.

In addition, the peritoneal function testing method of the present invention may further calculate a permeability coefficient for cell pores ($L_PS_C$) and an overall permeability coefficient ($L_PS$) from a Three-Pore Theory model while obtaining a ratio $L_PS_C/L_PS$ calculated using the $L_PS_C$ and the $L_PS$, and may use the $L_PS_C/L_PS$ ratio and a volume of water removal as indexes for the peritoneal function test.

As a result of keen investigation using extensive data collected from actual patients with peritoneal dialysis, the inventors of the present invention found that, when the value of $MTAC_{un/c}$ is closer to 1 (i.e. the values of $MTAC_{un}$ and $MTAC_c$ are closer to each other), the permeability of the patient's peritoneal function has been more deteriorated and the volume of water removal is less. That is, while conventional testing is able to analyze only the amount of solute removal and the volume of water removal, the use of $MTAC_{un}/_c$ of the present invention as described above enables examination of the future peritoneal function of a patient (a mechanism of deterioration in peritoneal function). The relation between $MTAC_{un}/_c$ and the future peritoneal function of a patient can be proven by empirical data obtained from patients actually having complications with peritonitis and patients likely to have the complications in the future.

Additionally, since $MTAC_{un}/_c$ is a dimensionless ratio, this parameter offers an advantage of being used in a mathematical model other than the Pyle-Popovich model, and furthermore allows a straightforward comparison between patients without requiring adjustment for variations in their physical attributes. Note that $L_PS_C/L_PS$ to be hereinafter described is also a dimensionless parameter, and offers an expanded versatility.

In the peritoneal function testing method of the present invention, the $MTAC_{un}/MTAC_c$ ratio and a volume of water removal may be used as indexes for the peritoneal function test.

Thus, checking values of $MTAC_{un}/_c$ and the volume of water removal virtually simultaneously enables a more detailed peritoneal function test to be made. To be more specific, for example, when the volume of water is low even if $MTAC_{un}/_c$ is favorable, a reduction in peritoneal function other than the solute transfer (i.e. mainly, the rate of transperitoneal water removal) can be determined. This leads to an examination of the adequacy of switching to an efficient dialysis procedure in which unnecessary use of antiphlogistic drugs for peritonitis is avoided (i.e. a switch to hemodialysis from peritoneal dialysis). When neither $MTAC_{un}/_c$ nor the volume of water removal is favorable, it is determined that peritoneal function has been severely damaged causing malignant failure, which allows a prompt transition of the dialysis procedure and quick countermeasures along with prescription of various antiphlogistic drugs. In the case when the volume of water removal is favorable while $MTAC_{un}/_c$ is low, it is determined that peritoneal function is in a benign failure mode (that is, although the aquaporins are sufficiently active, the small and large pores with reversibility are exhausted and temporarily deactivated), which raises consideration of the necessity of rest.

In addition, the peritoneal function testing method of the present invention may further calculate a permeability coefficient for cell pores ($L_PS_C$) and an overall permeability coefficient ($L_PS$) from the Three-Pore Theory model while obtaining a ratio $L_PS_C/L_PS$ calculated using the $L_PS_C$ and the $L_PS$, and may use the $L_PS_C/L_PS$ ratio and a volume of water removal as indexes for the peritoneal function test.

Herewith, a further detailed peritoneal function test can be achieved. To be more specific, a ratio ($L_PS_C/L_PS$) of water permeability coefficient of aquaporins to the overall water permeability coefficient is obtained from the Three-Pore Theory model. $L_PS_C/L_PS$ is a ratio representing the activity power of the aquaporins, which is believed to account for approximately 40% of the rate of transperitoneal water removal in pores in the capillary vessels of the peritoneum. The ratio taking a larger value means that the rate of the transperitoneal water removal is higher. A detailed diagnosis of peritoneal function is made possible by presenting a correlation of $L_PS_C/L_PS$ with $MTAC_{un}/_c$ or with the volume of water removal.

Furthermore, the present invention being a peritoneal function testing method using the Three-Pore Theory model may calculate a permeability coefficient for cell pores ($L_PS_C$) and an overall permeability coefficient ($L_PS$) while obtaining a ratio $L_PS_C/L_PS$ calculated using the $L_PS_C$ and the $L_PS$, and may use the $L_PS_C/L_PS$ ratio as an index for a peritoneal function test. Herewith, a specific function test on the rate of transperitoneal water removal can be achieved.

In this case, the use of $L_PS_C/L_PS$ described above and the volume of water removal as the test indexes achieves a detailed function test on the rate of transperitoneal water removal, which takes into consideration the activity power of the aquaporins.

BRIEF DESCRIPTION OF THE DRAWINGS

FIG. 6 shows input data items of the peritoneal test;

FIG. 7 shows input data items of the peritoneal test;

FIG. 16 shows a comparison between clinical data.

DETAILED DESCRIPTION OF THE INVENTION

1. First Embodiment

Here is described a first embodiment of the present invention.

The peritoneal dialysis planning apparatus of the present invention (i) computes two mathematical models known as peritoneal dialysis models, (ii) processes the results of computations, and (iii) outputs and displays the processed results. Peritoneal dialysis models include a macroscopic model called the Pyle-Popovich model and a microscopic model based on the Three-Pore Theory. First, a brief description of these models is provided here.

1.1 Mathematical Models of Peritoneal Dialysis

Figure 1:
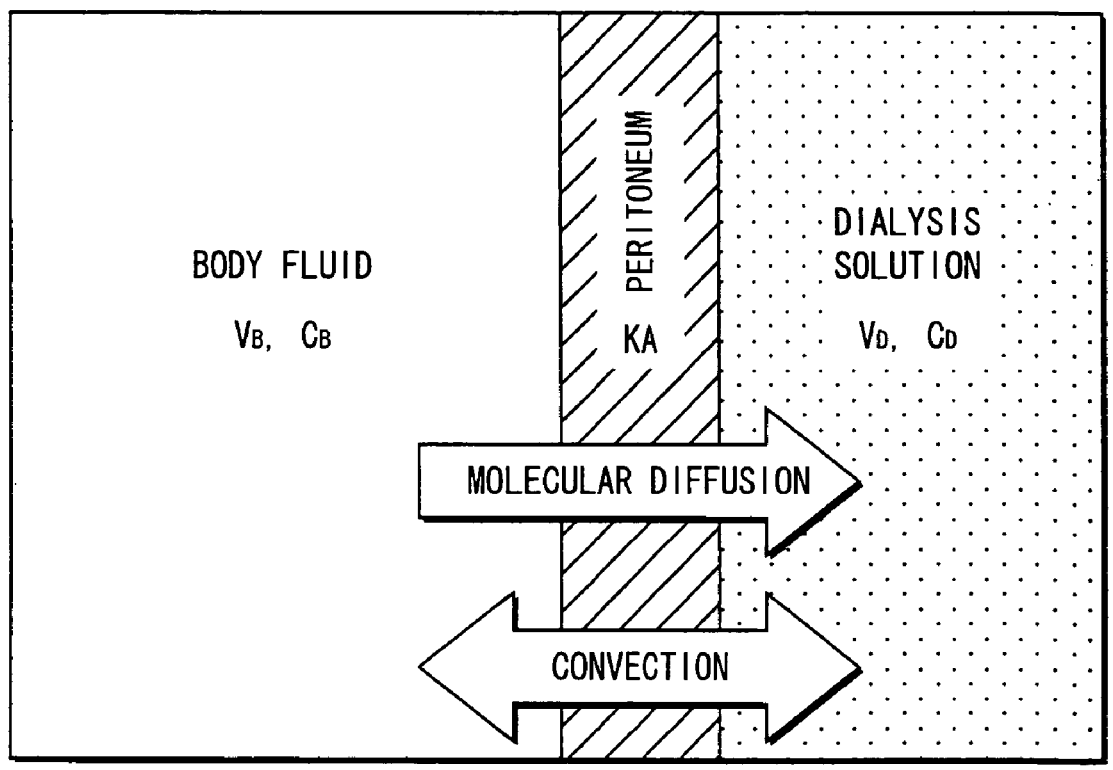
FIG. 1 is an explanatory diagram of a Pyle-Popovich model.

FIG. 1 is a cross-sectional view of a peritoneum, concisely illustrating the Pyle-Popovich model. The transfer of solutes from the body fluid to the dialysis solution via the peritoneum, which is assumed to be a homogeneous membrane, is represented by the sum of diffusion of solute molecules into the dialysis solution and convection (mass transfer due to water movement—that is, convective transport, and a back flow due to absorption of the lymphatic system in the peritoneum), as shown by arrows in the figure. This mathematical model can be expressed as the following set of formulae (1-1) to (1-8) of the mathematical expression I.

[Mathematical Expression I]

$$G - \frac{dV_B C_B}{dt} - C_{LR}C_B = \frac{dV_D C_D}{dt} = \dot{m} \quad (1\text{-}1)$$

$$\dot{m} = KA(C_B - C_D) + Q_U(1-\sigma)\overline{C} \quad (1\text{-}2)$$

$$\overline{C} = C_B - f(C_B - C_D) \quad (1\text{-}3)$$

$$f = \frac{1}{\beta} - \frac{1}{\exp(\beta)-1} \quad (1\text{-}4)$$

$$\beta = \frac{(1-\sigma)Q_U}{KA} \quad (1\text{-}5)$$

$$Q_U = a_1\exp(a_2 t) + a_3 \quad (1\text{-}6)$$

$$V_D(t) = V_D(0) + \frac{a_1}{a_2}[\exp(a_2 t) - 1] + a_3 t \quad (1\text{-}7)$$

$$V_B + V_D = V_B(0) + V_D(0) \quad (1\text{-}8)$$

where
t: time [min];
$C_{LR}$: residual renal function [mL/min];
$C_B$: concentration of a solute in blood [mg/mL];
$C_D$: concentration of a solute in the dialysis solution [mg/mL];
$V_B$: volume of body fluid [mL];
$V_D$: volume of the drained fluid [mL];
β: Peclet number [–];
$Q_U$: ultrafiltration rate (volume of ultrafiltration) [mL/min];
G: solute production rate [mg/min];
KA: overall mass transfer—area coefficient of peritoneum (MTAC) [mL/min];
σ: Staverman reflection coefficient [–];
$a_1$: empirical constant determining $Q_U$ [mL/min];
$a_2$: empirical constant determining $Q_U$ [1/min]; and
$a_3$: empirical constant determining $Q_U$ [mL/min].

Thus, the Pyle-Popovich model is based on a mass balance equation of individual solutes in the body fluid and those in the dialysis solution. In the Pyle-Popovich model, items calculated for each patient are: overall mass transfer—area coefficients KA of individual solutes, such as glucose, urea nitrogen, and creatinine (or alternatively, overall Mass Transfer-Area Coefficient, or MTAC); a (Staverman reflection coefficients); and water removal parameters, $a_1$, $a_2$ and $a_3$. Of them, the water removal parameters $a_1$, $a_2$ and $a_3$ are said to be particularly important for evaluating patient's capability of removing water (referred to as "the rate of transperitoneal water removal").

Empirical equations derived by Hume and Weyers can be used to calculate the volume of body fluid ($V_B$) (Hume et al., 1971). According to sex, the empirical equations are expressed in terms of height [HT (cm)] and weight [WT (Kg)] of a patient as follows:

Male: $V_B(0)$=–14.249+0.19678 HT+0.29571 WT; and

Female: $V_B(0)$=–9.9260+0.17003 HT+0.21371 WT.

In contrast with the Pyle-Popovich model, when peritoneal function is microscopically observed, there are considered to be partial variations in the permeability of each capillary vessel in the peritoneum. A peritoneal dialysis model on the basis of this perspective is the model of the Three-Pore Theory.

Figure 2:
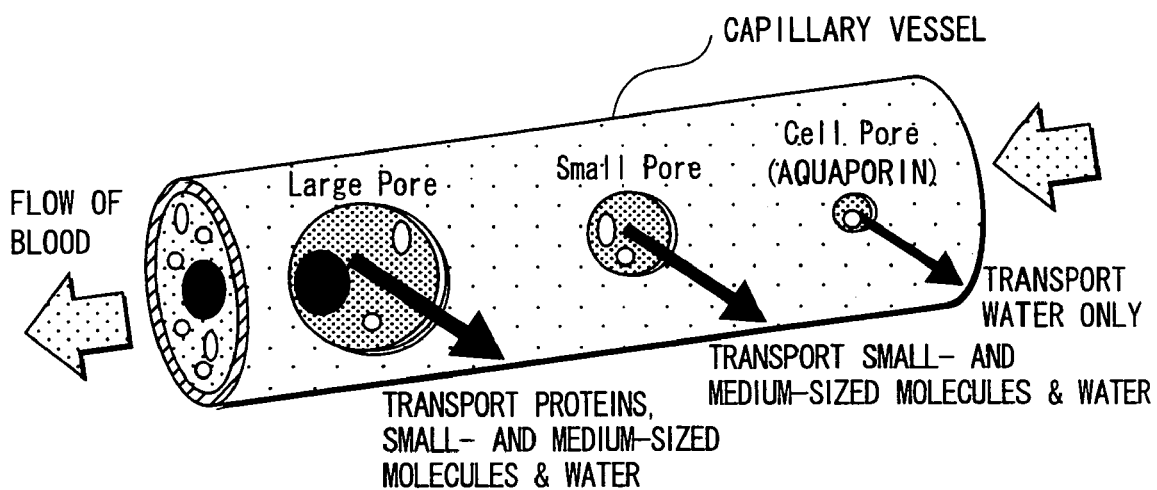
FIG. 2 is an explanatory diagram of a Three-Pore Theory model.

FIG. 2 is a schematic diagram of the capillary vessel, illustrating the model of the Three-Pore Theory. The Three-Pore Theory assumes that there are pores in three different sizes (large pores, small pores, and cell pores) in the capillary vessel. In this case, the pores act like a sieve because of the difference in size, and therefore the types and amounts of solutes which can pass through pores of specific sizes are regulated. For the same reason, pores of each size have a different contribution rate for water removal. Accordingly, in the Three-Pore Theory, the water transfer rates (filtration rates) are calculated for pores of large, medium, and small sizes, respectively, and the total water flow rate (total ultrafiltration rate) is then obtained. This mathematical model can be expressed as the following set of formulae (2-1) to (2-4) of the mathematical expression II, and the mathematical expressions III, IV and V.

[Mathematical Expression II]

$$Q_U = J_{VC} + J_{VS} + J_{VL} - J_{V\,lymph} \quad (2\text{-}1)$$

$$J_{VC} = L_P S_C \cdot (P_{capill} - \pi_{prot} - P_{ip} - \pi_{gluc} - \pi_{urea} - \pi_{Na} - \pi_{anions}) \quad (2\text{-}2)$$

$$J_{VS} = L_P S_S \cdot (P_{capill} - \sigma_S \pi_{prot} - P_{ip} - \sigma_S \pi_{gluc} - \sigma_S \pi_{urea} - \sigma_S \pi_{Na} - \sigma_S \pi_{anions}) \quad (2\text{-}3)$$

$$J_{VL} = L_P S_L \cdot (P_{capill} - P_{ip}) \quad (2\text{-}4)$$

where
$J_{VC}$, $J_{VS}$, $J_{VL}$: ultrafiltration rates for cell pores (aquaporins), small pores, and large pores, respectively [mL/min];
$J_{V\,lymph}$: lymphatic absorption flow rate [mL/min];
$L_P S_C$, $L_P S_S$, $L_P S_L$: water permeability coefficients for cell pores, small pores, and large pores, respectively;
$\pi_{prot}$, $\pi_{gluc}$, $\pi_{urea}$, $\pi_{Na}$, $\pi_{anions}$: osmotic pressures of protein, glucose, urea, sodium, and anions, respectively [mmHg];
$P_{capill}$: hydrostatic pressure [mmHg];
$P_{ip}$: hydrostatic pressure of the dialysis solution in the peritoneum [mmHg]; and
$\sigma_S$: reflection coefficient [–]

$$J_{V\,lymph} = -Q_U(t_{VAR}) = -L_P S[P_{ca} - P_{ip} - \sigma_{prot}(\pi_p - \pi_{ip})] \quad \text{[Mathematical Expression III]}$$

where $t_{VAR}$: time of when the crystalloid osmotic pressure gradient is lost [min]; and
$P_{ca}$: hydrostatic pressure exerted on capillary endothelial cells [mmHg].

$$V_D(t+\Delta t) = V_D(t) + \Delta t \cdot (J_{VC} + J_{VS} + J_{VL} - J_{lymph}) \quad \text{[Mathematical Expression IV]}$$

$$L_P S = L_P S_C + L_P S_S + L_P S_L \quad (5\text{-}1)$$

$$L_P S = \frac{0.070 \cdot \frac{A0}{\Delta x}}{23000} \quad (5\text{-}2)$$

where $L_P S$: water transport rate of the peritoneum (ultrafiltration coefficient) [mL/min/mmHg/1.73 m$^2$]; and
$A0/\Delta x$: area parameter [cm/1.73 m$^2$].

Note that $A0/\Delta x$ and $L_PS_C$ in the formulae (5-1) and (5-2) of the mathematical expression V are unknown parameters unique to each patient. Some methods for approximating these parameter values in the Three-Pore Theory model have been proposed, including the modified Powell method. Here, data is collected from dialysis solutions with two or more different osmotic pressures and the above-mentioned parameters are calculated using the modified Powell method. However, a different method may be employed for the calculation. Although the Pyle-Popovich model is capable of carrying out analysis by using two sets of data, the Three-Pore Theory model requires many more sets of data to find the parameters of $A0/\Delta x$ and $L_PS_C$ by repetitive calculations using the modified Powell method.

Note that cell pores are considered as aquaporins ($H_2O$ channels), and are essential since they make a contribution accounting for as much as 40% of the entire volume of water removal. The aquaporins have a very important correlation with the rate of transperitoneal water removal of a patient since they are irreversible and cannot be returned to the original state once being broken. Therefore, in dialysis treatments, how to retain the aquaporins without rendering them ineffective is a key issue to maintain peritoneal function.

Each of $L_PS$ items ($L_PS_C$, $L_PS_S$ and $L_PS_L$) is a water permeability coefficient, while $L_PS$ is called an overall water permeability coefficient. These coefficients taking large values indicates that the rate of transperitoneal water removal is high. Especially, a high value in $L_PS_C$ is considered that the rate of transperitoneal water removal of the patient has been maintained relatively well. Accordingly, it is very important to examine closely values of the water permeability coefficients when peritoneal function of patients is studied by using the Three-Pore Theory.

In the Three-Pore Theory, a current osmotic pressure can be obtained by updating the concentration gradient of each solute at the present moment, and also the water transfer rate is newly calculated. Then, further calculation together with the value of total peritoneal area is performed with respect to each patient, which enables construction of a detailed model of the solute transfer and the volume of water removal.

1.2 Configuration of Peritoneal Dialysis Planning Apparatus

Next is described the configuration of the peritoneal dialysis planning apparatus of the first embodiment according to the present invention. The peritoneal dialysis planning apparatus can be formed by implementing a program for executing a peritoneal dialysis testing method (a program for testing peritoneal function) on a general-purpose computer.

Figure 3:
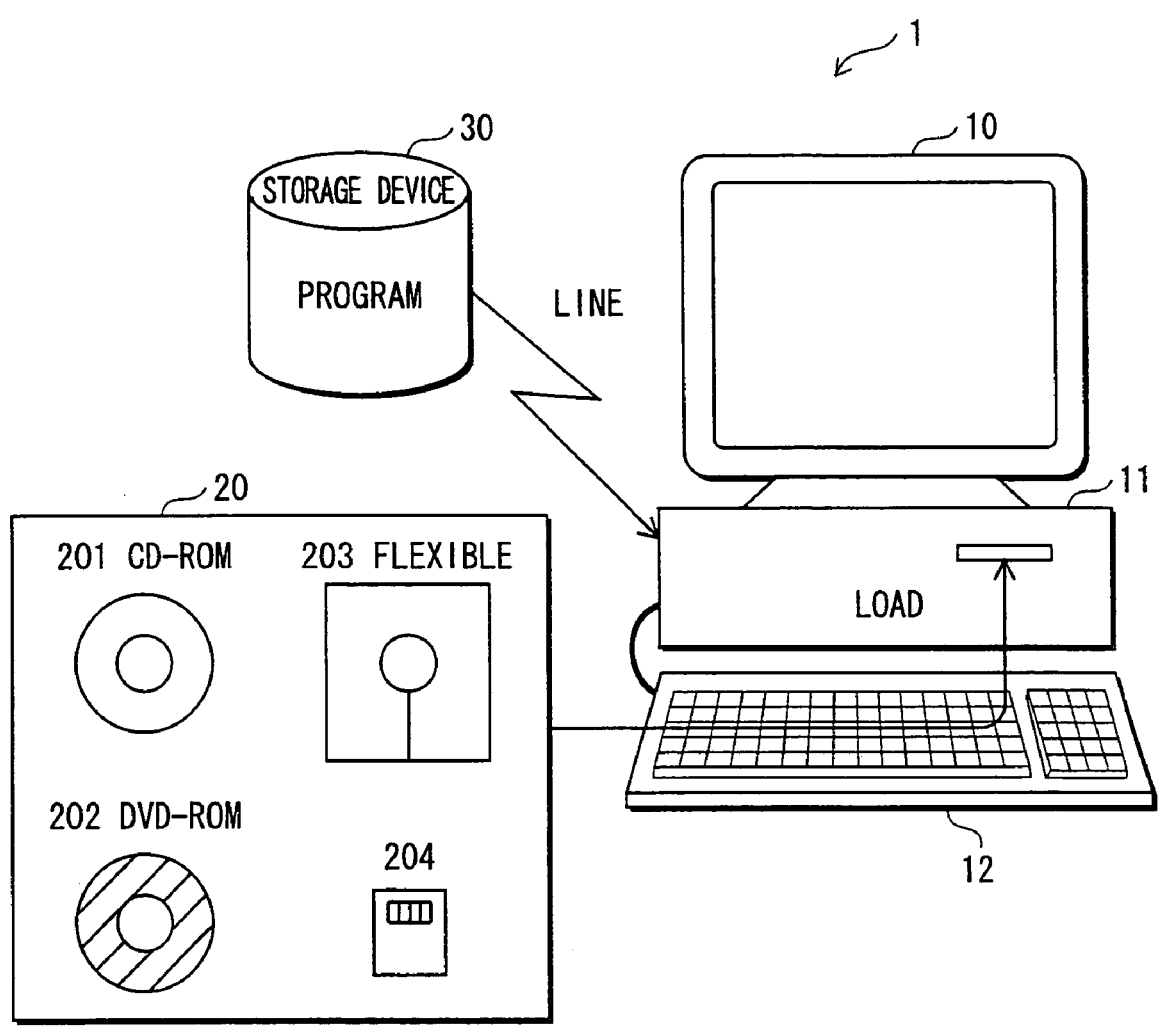
FIG. 3 is a schematic diagram of an applied example of the present invention—a peritoneal dialysis planning apparatus using a PC.

FIG. 3 shows a structural example of the peritoneal dialysis planning apparatus of the present invention. Here is shown a personal computer (PC) 1 comprising: a main body 11 having publicly known CPU, HD and memory therein; a keyboard 12 connected to the main body as input means; and a display 10 serving as data output means (display unit). The peritoneal function testing program of the present invention may be, for example, read to the PC 1 from various transportable recording media 20 (a CD-ROM 201, a DVD-ROM 202, a flexible disc 203, and a memory card 204), or may be read to the PC 1 from a storage device 30, such as a different server or PC, via a communication line. It is desirable that the peritoneal function testing program, once being read, be stored in the HD of the PC 1, along with patient's data.

The peritoneal dialysis planning apparatus uses a range of data obtained from a patient in a general test (for example, Peritoneal Equilibration Test, or PET) as input data. The CPU of the PC 1 computes mathematical models of peritoneal function (the Pyle-Popovich model, or both the Pyle-Popovich model and the Three-Pore Theory model), and performs processing specific to the first embodiment on data pertaining to the concentration of each solute, the volume of water removal and the like which are obtained as a result of computation. Then, the CPU presents the processed data on the display 10. The presented contents on the display 10 assist consideration of the future peritoneal dialysis planning. Herewith, the peritoneal dialysis planning apparatus of the present invention is characterized in that the state of peritoneal function over time (a mechanism of deterioration in peritoneal function) can be tested in an appropriate manner.

Note that the peritoneal dialysis planning apparatus has an advantage of making an effective use of conventional devices and data from the past, not requiring other special devices, calculation methods, new data which has previously never been used or the like, to perform the function.

1.3 Configuration of Peritoneal Function Testing Program

Figure 4:
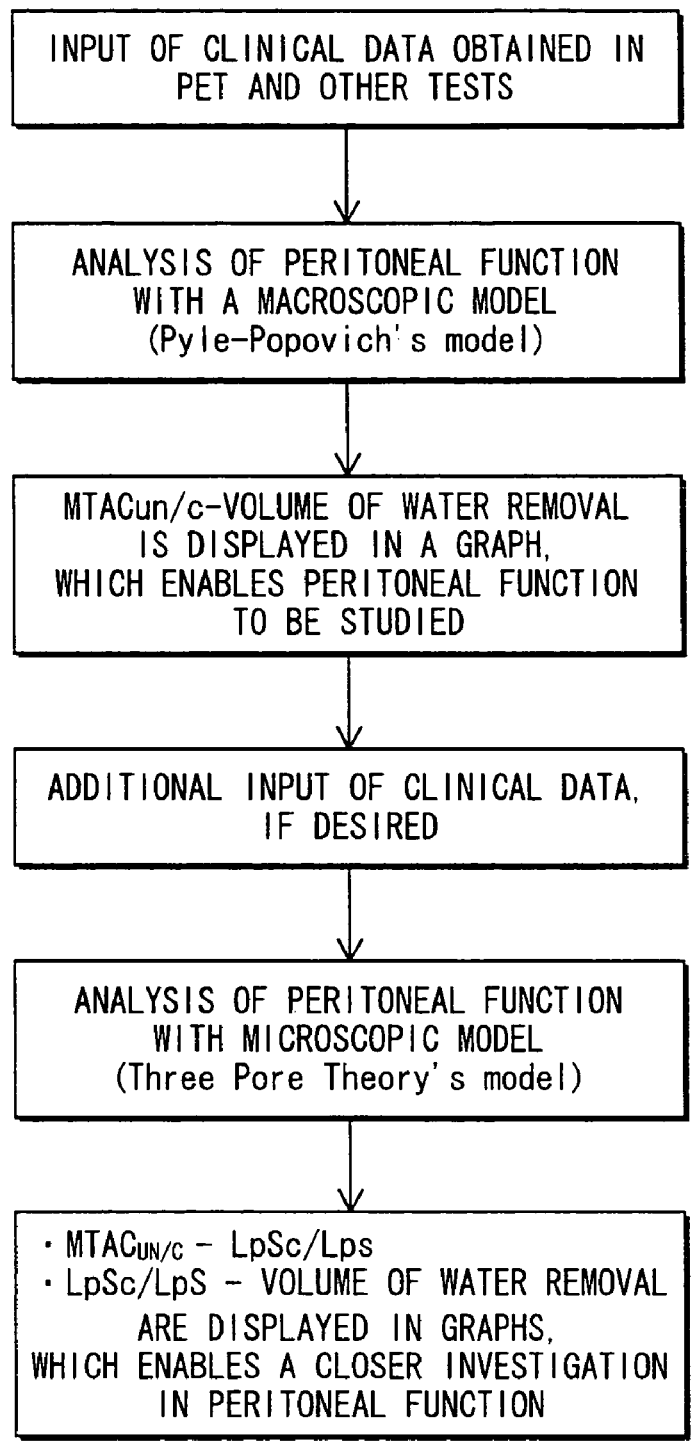
FIG. 4 shows a flow of an embodiment using the peritoneal dialysis planning apparatus.

The peritoneal function testing program implemented on the PC 1 is configured to be generally executed in the following sequence. FIG. 4 shows a sequence of the program, from input of the data to display of the peritoneal function.

As shown in the figure, first, patient's clinical data required for the peritoneal function test is input to the PC 1. The program becomes executable after the data is input, and computes the Pyle-Popovich model according to an operator's direction. The MTAC ratio ($MTAC_{un/c}$) of urea nitrogen and creatinine is obtained by using parameters acquired from the computation, such as solute concentrations and the volume of water removal, and a graph showing a correlation between $MTAC_{un/c}$ and the volume of water removal is presented on the display 10. This enables the operator to conduct a study on peritoneal function. The main feature of the present invention is to use $MTAC_{un/c}$ and $L_PS_C/L_PS$—which is described hereinafter—as indexes of the peritoneal function test. Effectiveness of $MTAC_{un/c}$ and details about $MTAC_{un/c}$ and $L_PS_C/L_PS$ are described in more depth when the operational sequence is discussed.

The program can complete the work once when the graph of the correlation between $MTAC_{un/c}$ and the volume of water removal is presented on the display 10. However, the program performs further computation to make a more precise investigation for the peritoneal function test at operator's request. In this case, the PC 1 checks if the amount of the obtained data sets is sufficient (specifically speaking, three or more data sets in relation to dialysis solutions with multiple osmotic pressures are required), and then computes the Three-Pore Theory model. By using water permeability coefficients and other parameters obtained from the computation, a correlation between $MTAC_{un/c}$ and $L_PS_C/L_PS$ together with the volume of water removal computed earlier as well as a correlation between $L_PS_C/L_PS$ and the volume of water removal are displayed in graphs. This enables the operator to conduct a detailed study on peritoneal function.

Regarding the patient's data to be input, it is desirable that all items required to calculate both the Pyle-Popovich model and the Three-Pore Theory model be prepared in sufficient quantities and set ready to be input to the PC 1 prior to the program being run, which allows prompt computations.

1.4 Practical Example

In order to make the apparatus work, data obtained from a patient is required. A method for acquiring the data is first described prior to a description of the apparatus operations.

1.4.1 Acquisition and Input of Clinical Data

Figure 5:
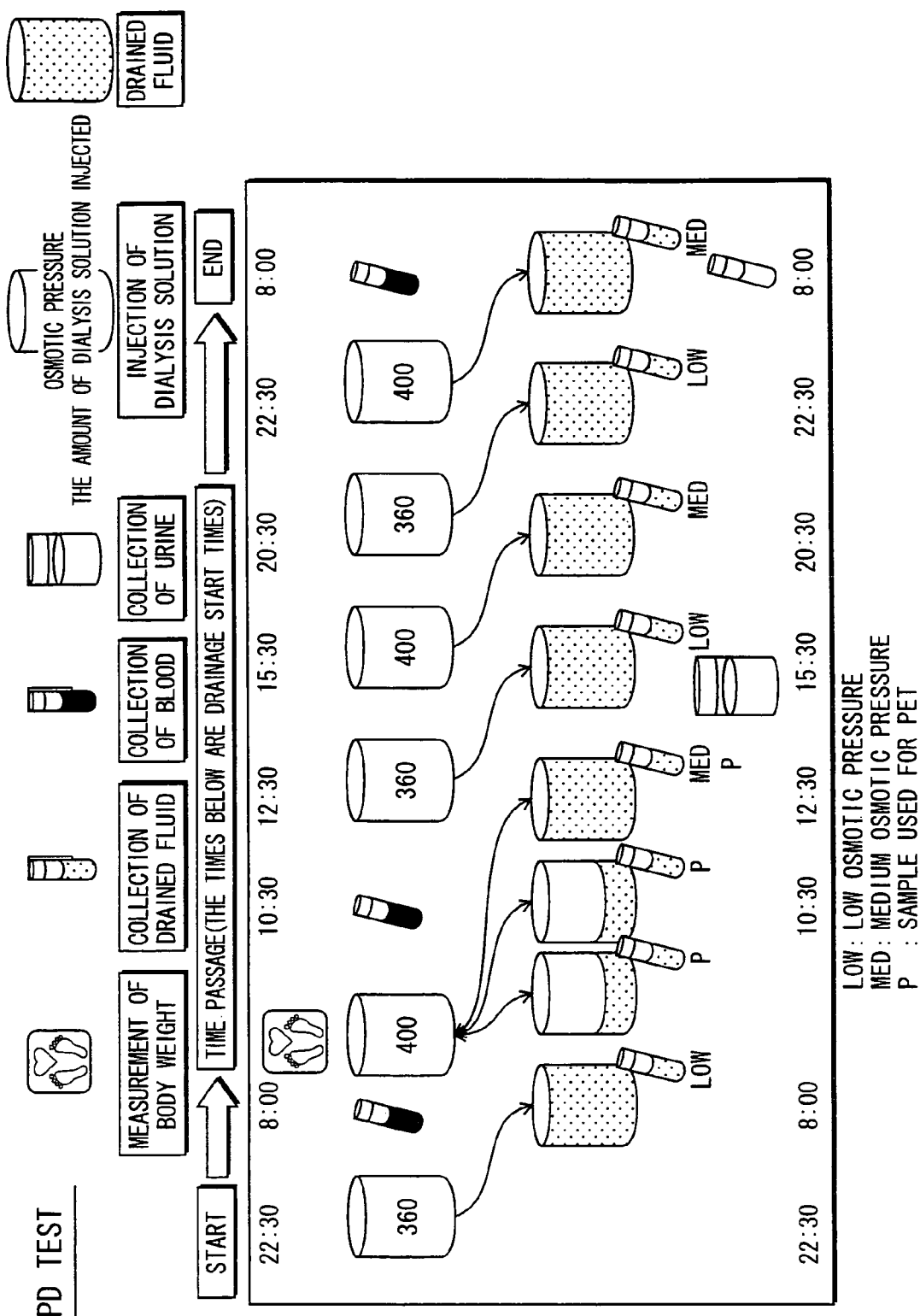
FIG. 5 shows an example of a time chart of a peritoneal test.

Here are shown a procedure for the above-mentioned peritoneal function test (clinical test) of the present invention and an example of data acquisition steps. FIG. 5 shows the steps for the data acquisition. In the data acquisition steps, dialysis solution exchange, which starts in the evening of a previous day, is performed on a patient six times in total at intervals of 10.5 hours, 4 hours, 3 hours, 5 hours and 2 hours, by alternately using dialysis solutions both having 2 litters in volume but one with an osmotic pressure of 360 (mOsm/kg-solvent) while the other having an osmotic pressure of 400 (mOsm/kg-solvent). Here, a blood sample is taken on a regular schedule, and a urine sample is collected while the concentration of each solute is checked. The osmotic pressures of the dialysis solutions and the number of exchanges can take values other than the above. Note that the example shown here uses dialysis solutions having two different osmotic pressures, which is necessary for computing the formulae of both the Pyle-Popovich and the Three-Pore Theory. Here, the computation of the Pyle-Popovich formulae requires at least two different sets of data on drained fluids with each osmotic pressure, while the computation of the Three-Pore Theory formulae requires at least three different sets of data for drained fluids with each osmotic pressure, and therefore appropriate settings should be configured to comply the data acquisition.

The items of clinical data obtained through the data acquisition steps include the height, weight and sex of the patient, the amount of collected urine, and the concentration of each solute in urine (urinary urea nitrogen, urinary creatinine, urinary protein, and urinary sodium), as shown in FIGS. 6 and 7. The exact same tables of the figures are presented on the display 10 of the peritoneal dialysis planning apparatus 1, and each item can be input via the input means (i.e. keyboard) 12. The operator of the PC 1 enters the input items of FIGS. 6 and 7.

The input items include the concentrations of blood-total protein, albumin, serum creatinine, urea nitrogen, glucose, sodium, chloride and so on, obtained from the blood samples. In this case, blood sampling is performed three times and therefore concentration measurements are repeated with respect to each input item when a blood sample is collected, and then the values are entered.

Note that, in the present embodiment, the presentation of a graph becomes possible by using numerical values obtained from at least three data sets on the drained fluids.

In terms of the drained fluids, the glucose concentration, the total weight of medical solution, the drainage start time, the patient's weight after the drainage, the finish time of injecting a dialysis solution and so on are recorded.

1.4.2 Operation of Peritoneal Dialysis Planning Apparatus

Once the input of the above individual pieces of data to the peritoneal dialysis planning apparatus is completed, the program of the peritoneal dialysis planning apparatus (a peritoneal function testing program) can be executed.

Figure 8:
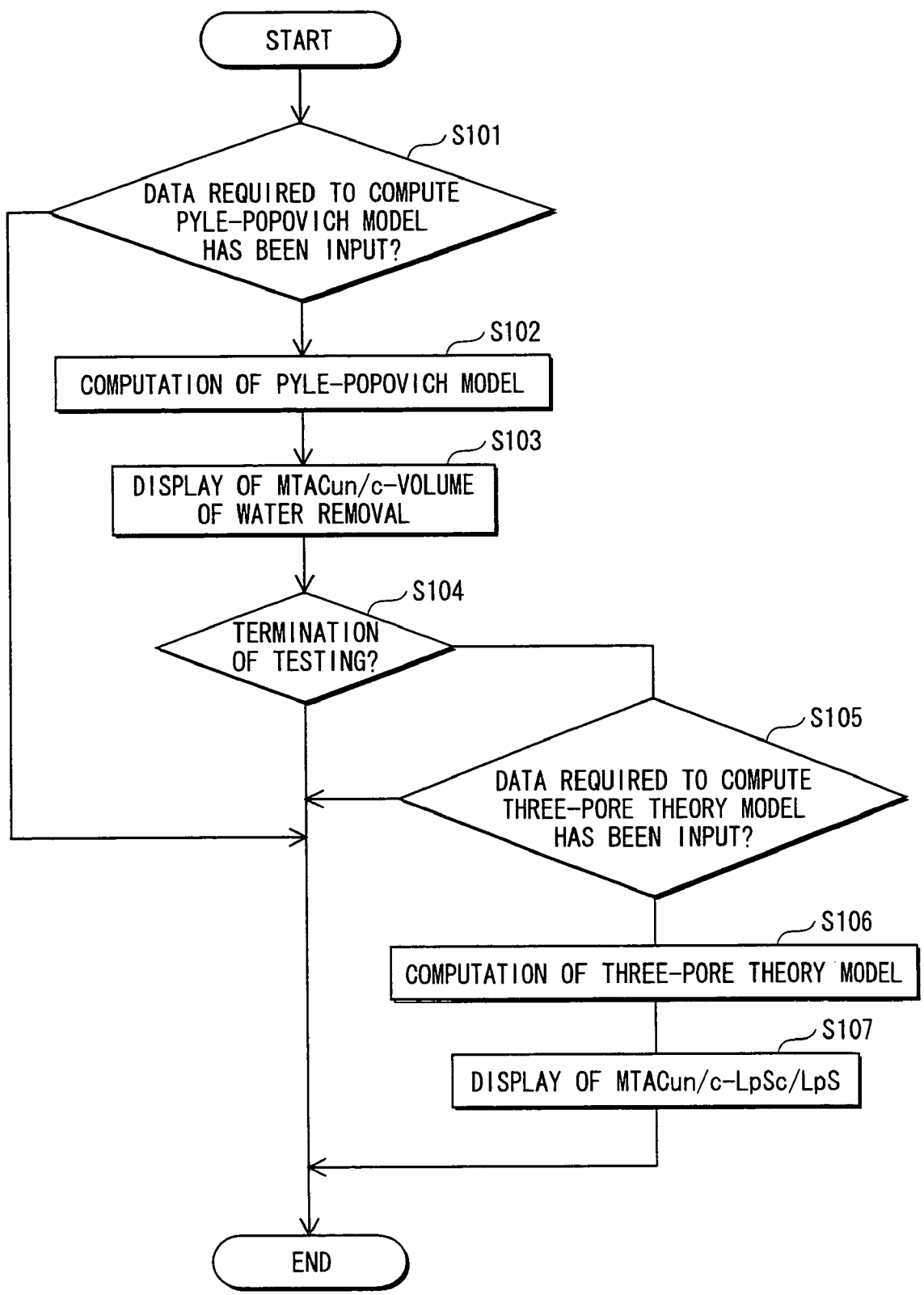
FIG. 8 is a flow diagram of a peritoneal function program of the present invention.

FIG. 8 is a flow diagram showing exemplified steps of the peritoneal function testing program.

According to the figure, the program is first launched on the PC 1, which then judges whether or not data required to compute the Pyle-Popovich model has been input (Step S101).

If the input data has sufficiently been provided, the PC 1 computes the Pyle-Popovich model shown in the above mathematical expression I, based on the input patient's data (Step S102). This computation determines the overall mass transfer—area coefficients for urea nitrogen ($MTAC_{un}$) as well as for creatinine ($MTAC_c$), the volume of water removal and so on. Note that how to compute the simultaneous equations of the Pyle-Popovich model is described in Japanese Laid-Open Patent Application Publication No. 2000-140100. Here, the PC 1 characteristically calculates the ratio ($MTAC_{un}/c$) of $MTAC_{un}$ to $MTAC_c$ obtained from the computation of the Pyle-Popovich model, and presents a graph showing the correlation between the $MTAC_{un}/c$ ratio and the volume of water removal on the display 10 (FIG. 9) (Step S103).

Focusing on the transfer rate of each solute (MTAC) derived from the Pyle-Popovich model, the present inventors have for the first time discovered the $MTAC_{un}/c$ ratio that is a mass transfer parameter effectively applicable as a dramatically more precise peritoneal function testing and therapeutic indication of individual patients.

In other words, $MTAC_{un}$ and $MTAC_c$ respectively are quantitative indexes of publicly known overall mass transfer—area coefficients, and each value indicates, only on a piecemeal basis, the peritoneal function of a patient of when data was obtained. Doctors cannot comprehend details of the state of patient's peritoneal function based on these numerical values alone. In addition, as indexes for evaluating the dialysis efficiency (i.e. quantitatively evaluating the clear space), clearance, Kt/V and the like are generally used in order to determine the excess or deficiency of the amount of a dialysis solution. However, the concepts of these indexes are dissimilar, and therefore it is difficult to study peritoneal function in a comprehensive manner.

However, $MTAC_{un}/c$ indicates that, when the value is closer to 1 (i.e. the values of $MTAC_{un}$ and $MTAC_c$ are closer to each other), the patient has a higher possibility of having complications with peritonitis or having such complications in the future, or the patient has a peritoneum with deteriorated function. In all of these cases, the introduction of hemodialysis is considered as a countermeasure. The validity of such judgment can be proved by empirical data obtained from patients actually having complications with peritonitis and patients likely to have the complications in the future (data showing that patients having complications with peritonitis have a deteriorated level of permeability of the peritoneum is provided in a paper (*Advances in Peritoneal Dialysis*, vol. 18, pp. 144-148, 2002)). That is, although conventional testing is capable of analyzing only quantitative indexes, the present invention is able to perform time-lapse diagnoses of the peritoneum. Additionally, since $MTAC_{un}/c$ is a dimensionless ratio, the parameter need not be adjusted for variations in physical attributes of individual patients, and furthermore offers a high versatility since it can be used in the Pyle-Popovich model as well as formulae based on other concepts. Note that $L_PS_C/L_PS$, as will hereinafter be described, is also a dimensionless parameter, and offers an expanded versatility.

Figure 9:
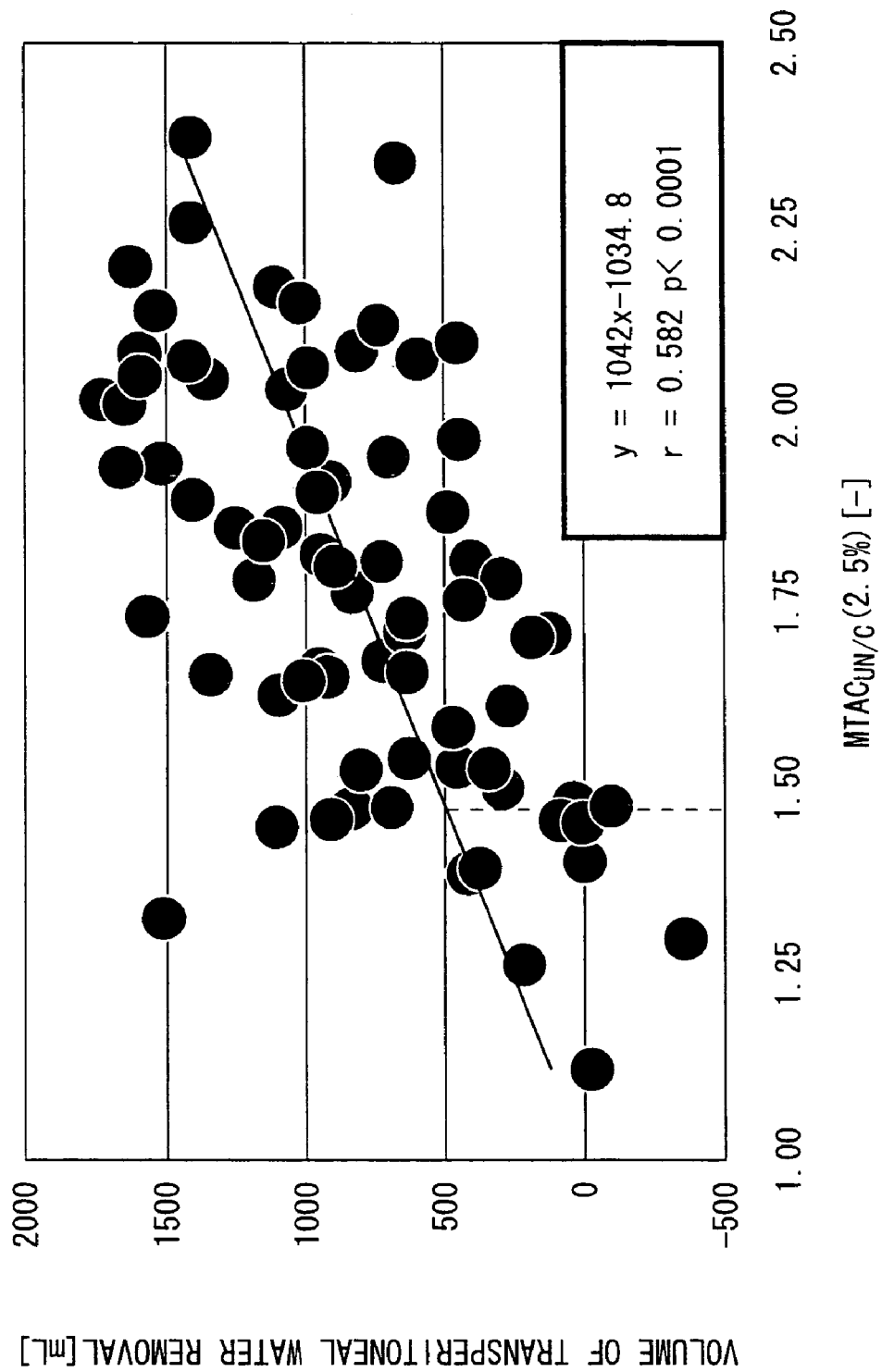
FIG. 9 is a graph showing a correlation between $MTAC_{un}/_c$ and the volume of water removal (sample)

Besides, the first embodiment is capable of performing more detailed testing on peritoneal function by making a graph plotting $MTAC_{un}/c$ against the volume of water removal, as shown in FIG. 9. Here, a dialysis solution with a glucose concentration of 2.5% is used, and the volume of water removal is plotted on the vertical axis while $MTAC_{un}/c$ is plotted on the horizontal axis. According to the graph, values of $MTAC_{un}/c$ and the volume of water removal of when the data was obtained can be checked virtually simultaneously. Therefore, for example in the case when the volume of water removal is low, even if $MTAC_{un}/c$ is favorable, a reduction in peritoneal function other than the solute transfer (i.e. mainly, the rate of transperitoneal water removal) can be determined. This leads to an examination of the adequacy of switching to an efficient dialysis procedure in which unnecessary use of antiphlogistic drugs for peritonitis is avoided (i.e. a switch to hemodialysis from peritoneal dialysis). When neither $MTAC_{un}/c$ nor the volume of water removal is favorable, it is determined that peritoneal function has been severely damaged causing malignant failure, which allows a prompt transition of the dialysis procedure and quick countermeasures along with prescription of various antiphlogistic drugs. In the case when the volume of water removal is favorable, while $MTAC_{un}/_c$ is low, it is determined that peritoneal function is in a benign failure mode (that is, although the aquaporins are sufficiently active, the small and large pores with reversibility are exhausted and temporarily deactivated), which raises consideration of the necessity of rest.

Note that FIGS. 9 to 12 plot actual measurements obtained from multiple patients and show the distributions. A line in each graph represents a regression line of the graph. Values of y, r and p in each graph are numerical values indicating characteristics of the measurement distribution. Such lines provide indications of peritoneal function of a patient. (For example, assume that the volume of water removal of a patient is located below the line. This means that the patient has a lower rate of transperitoneal water removal than the average.) In addition, such lines may offer an advantageous effect when data of multiple patients or multiple pieces of time-lapse data of a single patient are displayed.

Thus, the first embodiment is able to obtain information on the mechanism of deterioration in peritoneal function of a patient from various angles by making a graph of a correlation between $MTAC_{un}/_c$ and the volume of water removal, which allows appropriate evaluations. The data of FIG. 9 can be derived only from the Pyle-Popovich model, and thus there is an advantage of obtaining the data by comparatively simple testing and computations. In addition, since $MTAC_{un}/_c$ is acquired from $MTAC_{un}$ and $MTAC_c$—existing data which has conventionally been collected, the present invention makes an effective use of the past data without wasting them, and utilizes them as more specific and adequate testing parameters.

Note that a graph to be displayed in Step S103 is here set to the graph of $MTAC_{un}/_c$ v.s. the volume of water removal. However, it is also possible to display data of $MTAC_{un}/_c$ alone by selection from the display setting items of the program.

In the comparatively simple peritoneal function testing, the graph of FIG. 9 showing a correlation between $MTAC_{un}/_c$ and the volume of water removal allows some degree of examination, as described above. Consequently, the PC 1 prompts the operator to decide whether or not to complete the testing (Step S104). At this point, if the operator desires to have more detailed peritoneal function testing, the PC 1 executes the program to proceed to the next step.

In the following step, the PC 1 checks if a sufficient amount of data is present (Step S105). This step is taken in order to see if the amount of data is enough to solve Three-Pore Theory model. When there is enough data (that is, if data on dialysis solutions of two or more osmotic pressures has been input), the PC 1 computes the Three-Pore theory model shown in the above mathematical expressions II to V, based on the input patient's data (Step S106). Here, the PC 1 characteristically calculates the ratio ($L_PS_C/L_PS$) of the water permeability coefficient of aquaporins to the overall water permeability coefficient, and makes a graph of a correlation between, e.g., $L_PS_C/L_PS$ and previously calculated $MTAC_{un}/_c$, which is then presented on the display 10 (FIG. 10) (Step S107).

Note that, although the graph of $MTAC_{un}/_c$ v.s. $L_PS_C/L_PS$ (FIG. 10) is presented here in the process flow, a graph desired by the user—i.e. any one of $MTAC_{un}/_c$ v.s. $L_PS_C/L_PS$ (FIG. 10), $MTAC_{un}/_c$ v.s. $L_PS_C/L_PS$ with peritoneal function states labeled (FIG. 11), and $L_PS_C/L_PS$ v.s. the volume of water removal (FIG. 12)—can be presented on the display 10 by modifying the display setting of the program.

Thus, the first embodiment is capable of performing further detailed peritoneal function testing by calculating the ratio ($L_PS_C/L_PS$) of the dynamic water permeability coefficient of aquaporins to the overall water permeability coefficient obtained from the computations of the Three-Pore Theory. The $L_PS_C/L_PS$ ratio represents the activity power of the aquaporins, which is believed to account for approximately 40% of the rate of transperitoneal water removal in pores in the capillary vessels of the peritoneum. The ratio taking a larger value means that the rate of the transperitoneal water removal is higher. A detailed diagnosis of peritoneal function is made possible by presenting a correlation of $L_PS_C/L_PS$ with $MTAC_{un}/_c$ or with the volume of water removal.

Namely, for example, when the value of $L_PS_C/L_PS$ is not favorable, the reason is thought to be attributable to a decrease in activity of the aquaporins. In general tests of the rate of transperitoneal water removal, on the other hand, a patient is examined mainly based on data of an apparent volume of water removal obtained in CAPD. In this case, if the volume of water removal is low, multiple possible causes as follows can be in fact deduced, making it difficult to determine which of the following causes is/are the actual cause:

A: water is not drained out since the catheter tip inserted into the peritoneum is physically blocked or malpositioned (external factor);

B: the lymphatic system of the peritoneum has an elevated level of reabsorption capability; and C: actual peritoneal function (the rate of transperitoneal water removal) has been reduced.

Of them, when A is the real cause, the blockage in the catheter is removed or the position is corrected, while anti-inflammatory agents are administered into the lymphatic system when B is the cause. If the cause is C, dialysis modality is switched from peritoneal dialysis to hemodialysis. Thus, the ways of handling the situation are much different depending on the real cause. In addition, when both B and C are the causes, the patient may possibly have complications with peritonitis or encapsulated peritoneal sclerosis, and therefore much consideration has to be given to how to treat the patient.

Thus, conventional methods of testing peritoneal function do not fully allow critical judgments to be made to determine appropriate treatments for patients, and therefore, there is still room for improvement. On the other hand, the present invention using $L_PS_C/L_PS$ that is a parameter independent of the above causes A and B is capable of comprehending the rate of transperitoneal water removal of a patient with dramatically improved accuracy. Here, $L_PS_C/L_PS$ of the present invention is calculated based on data collected from a patient, and determined as a dynamic ratio unique to an individual patient. With regard to $L_PS_C/L_PS$, there are conventional systems in which peritoneal function testing is carried out by using the ratio (for example, a peritoneal function testing system manufactured by Gambro). However, the ratio is specified as a fixed value (1) and does not reflect specific peritoneal function of each patient. A method of using the dynamic $L_PS_C/L_PS$ ratio as a testing index was constructed, for the first time, in the present invention.

Figure 10:
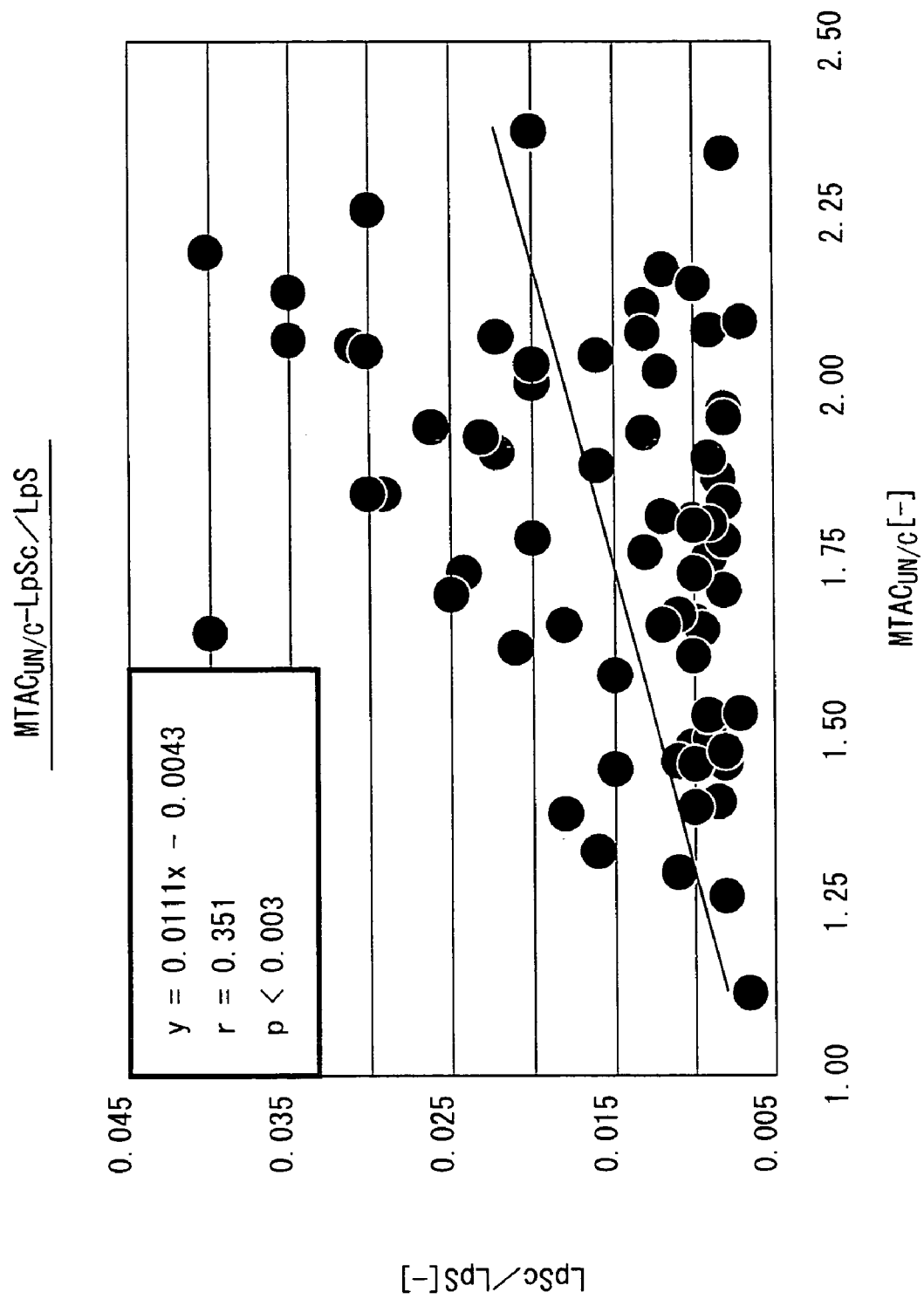
FIG. 10 is a graph showing a correlation between $MTAC_{un}/_c$ and $L_PS_C/L_PS$ (sample)

Here, FIG. 10 presented on the display 10 in Step S107 is a graph plotting $MTAC_{un}/_c$ against $L_PS_C/L_PS$, which are acquired by computing the Pyle-Popovich model and the Three-Pore Theory model. In FIG. 10, $L_PS_C/L_PS$ indicates a more accurate rate of transperitoneal water removal than an apparent volume of water removal obtained by CAPD. It can therefore be said that the graph shows data with a higher level of accuracy than the data of FIG. 9, which is derived only from the Pyle-Popovich model described above. The present invention also has an advantageous effect of allowing a choice between computing only the Pyle-Popovich model or computing the model in combination with the Three-Pore Theory model, depending on whether a higher priority is placed on simplicity or accuracy when peritoneal function of a patient is examined.

Figure 11:
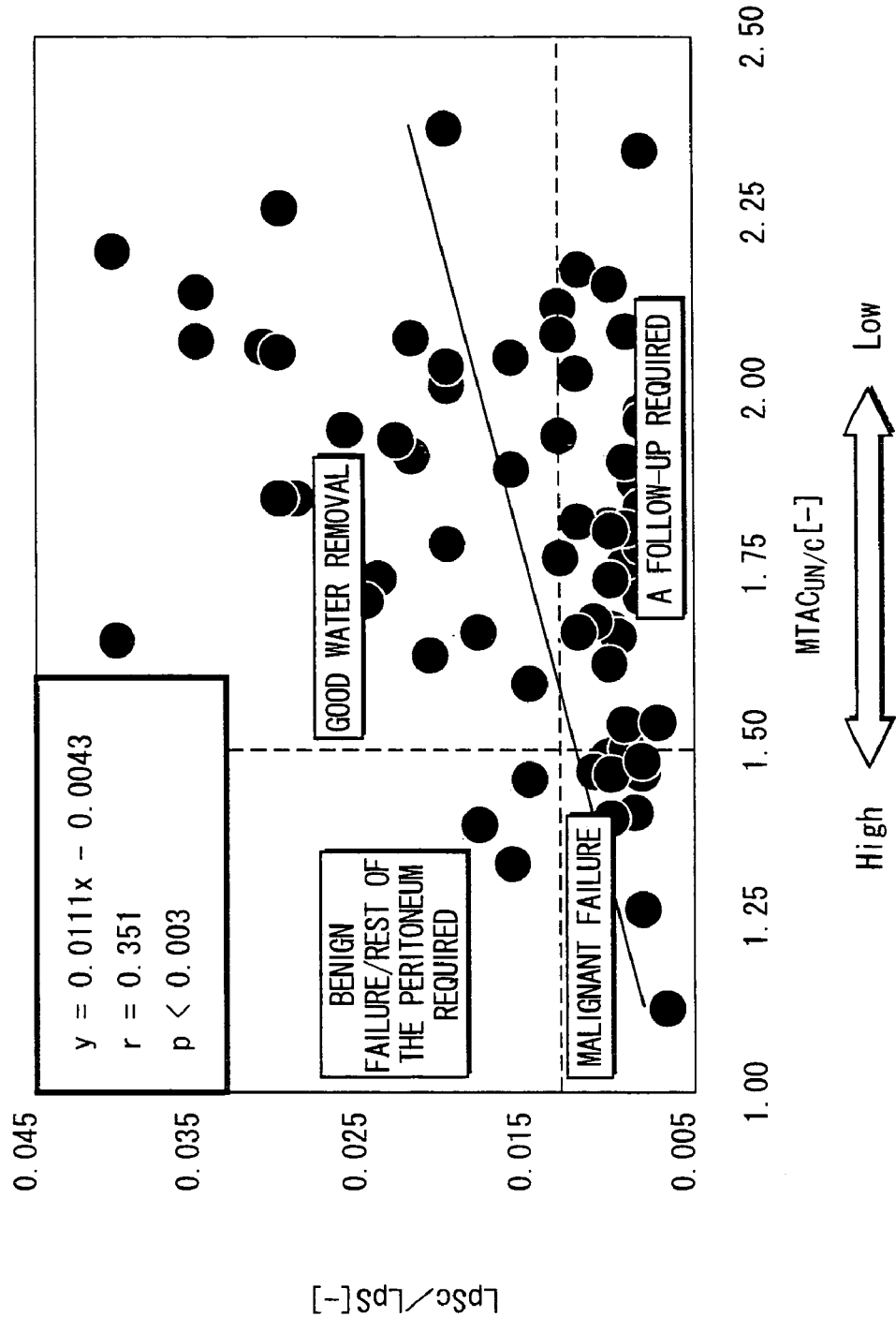
FIG. 11 is a graph showing a correlation between $MTAC_{un}/_c$ and $L_PS_C/L_PS$ (with a display of areas according to peritoneal function diagnoses) (sample)

Note that it is effective to roughly divide the area of a graph into sub-areas according to states of peritoneal function when the graph is displayed since this provides a rough indication for the location of obtained data in the graph. FIG. 11 shows an example in which the area of the coordinates of the graph in FIG. 10 above is divided into sub-areas of "good water removal", "benign failure/rest of the peritoneum required", "a follow-up required" and "malignant failure", according to the states of peritoneal function. Here, the boundary on the horizontal axis between "good water removal" and "benign failure/rest of the peritoneum required" and the boundary on the vertical axis between "malignant failure" and "benign failure/rest of the peritoneum required" are determined individually by likely values that $MTAC_{un/c}$ and $L_PS_C/L_PS$ would take when the volume of water removal is approximately 500 mL (in general, when the volume of water removal reaches 500 mL, switching from a peritoneal dialysis to hemodialysis is recommended). The present invention may, thus using such categories, allow a rough assessment of the state of peritoneal function to be made according to the location of the collected data in the category map. It is a matter of course that the position of each boundary, the type of line used to represent the data in a category map, words used to label the categories can be changed accordingly.

Figure 12:
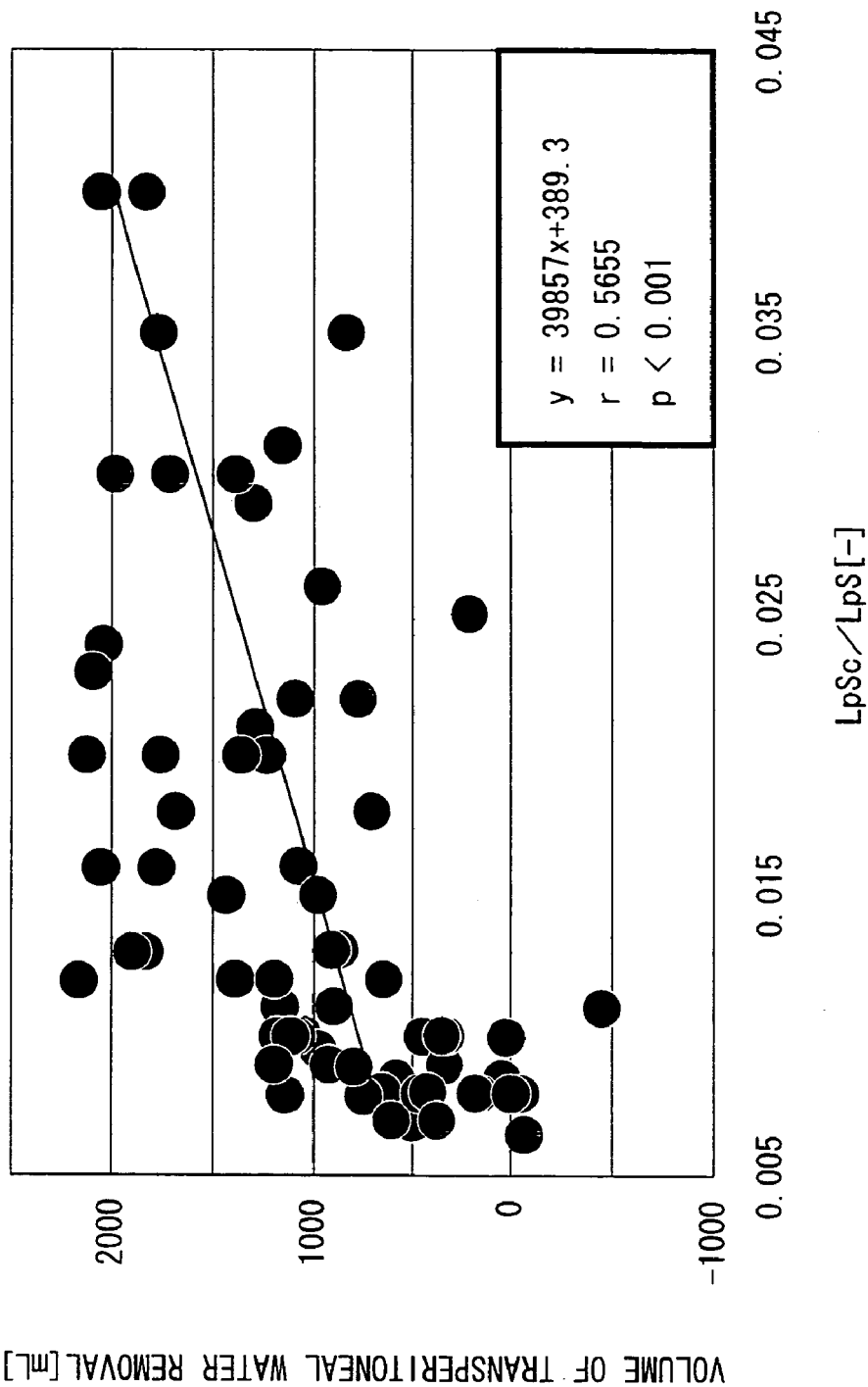
FIG. 12 is a graph showing a correlation between $L_PS_C/L_PS$ and the volume of water removal (sample)

$L_PS_C/L_PS$ basically has a property of being proportional to the rate of transperitoneal water removal. Therefore, if a graph is created with these parameters plotted on the horizontal and vertical axes, respectively, the possibility that water removal is not properly being performed can be assessed when there is no proportional relationship between $L_PS_C/L_PS$ and the volume of water removal of the obtained data. FIG. 12 is a graph showing a correlation between $L_PS_C/L_PS$ and the volume of water removal in such a case. According to a graph like this, for example, when $L_PS_C/L_PS$ is favorable while the volume of water removal is low, the following possibilities can be considered: the lymphatic system has an elevated level of reabsorption capability; and water cannot be removed since the catheter is blocked, malpositioned, or contaminated. Accordingly, it is made possible to prescribe a medicine to reduce the elevated level of the reabsorption by the lymphatic system when the former is the cause, or to advise the patient on an appropriate CAPD procedure and instrument management when the latter is the cause. The PC 1 here completes the entire process flow.

Note that, in the steps for displaying data (Steps S103 and S107) described above, it can also be made possible to provide selection of whether or not the above-described boundaries roughly indicating states of peritoneal function and words used to label the categories are displayed on the graph together with the patient's data.

Once displaying a graph desired by the operator in Step S107, the PC 1 can terminate the program.

2. Second Embodiment

2.1 Main Characteristics of Second Embodiment

A second embodiment of the present invention is described next.

The configuration of a peritoneal dialysis planning apparatus and basic operations of a peritoneal function testing program (including items on the screen display) according to the second embodiment are the same as those in the first embodiment, and therefore the following discusses the second embodiment, focusing on differences from the first embodiment.

The second embodiment is characterized by achieving a peritoneal function test of higher precision by applying, in the peritoneal function testing program installed on the PC 1, a Genetic Algorithm (GA) to parameter values obtained from the computation of the Pyle-Popovich model to thereby make them an optimal solution for actual measurements of clinical data in advance, and then introducing the solution to the formulae of the Three-Pore Theory.

In addition, by adopting the Genetic Algorithm, the computation of the Pyle-Popovich model becomes simplified and a reduction in the quantity of clinical data required is achieved. This in turn brings about an effect of easing the burden of patients and data examiners of when clinical data is collected.

Note that the Genetic Algorithm itself is a well-known mathematical model used as a search technique to find an optimal solution. The details are discussed in, for example: "*Iden Algorithm to Saiteki-ka* (Genetic Algorithm and Optimization)" (edited by the Institute of Systems, Control and Information Engineers, and published by Asakura-syoten on 15 Apr. 1998); "*Iden-teki Programming Nyumon* (Introduction to Genetic Programming)" (by Hitoshi IBA, published by University of Tokyo Press in July 2001); and "*Iden Algorithm to Neural Network—Scheduling to Kumiawase Saiteki-ka* (Genetic Algorithm and Neural Network—Scheduling and Combined Optimization)" (edited by Denki-gakkai Iden Algorithm nado Kumiawase Saiteki-ka Syuho Ohyo Chosa Senmon Iinkai (Expert Committee on Investigation of Genetic Algorithm and Other Combined Optimization Method Application at the Institute of Electrical Engineers of Japan), published by Corona-sha in January 1998).

Specifically speaking, the second embodiment deals with overall mass transfer—area coefficients KA of individual solutes—such as, glucose, urea nitrogen and creatinine—obtained from the computation of the Pyle-Popovich model. In other words, $MTAC_{glc}$ (MTAC of glucose), $MTAC_{urea}$ ($MTAC_{un}$), and $MTAC_{crea}$ ($MTAC_c$), and furthermore a water permeability coefficient ratio $_rL_PS_C$ are treated as discrete parameters varying independently of one another. The ratio $_rL_PS_C$ is, as shown in the mathematical expression VI below, directly obtained by transforming the formula (5-1) of the above mathematical expression V.

[Mathematical Expression VI]

$$_rL_PS_C = \frac{L_PS_C}{L_PS}$$

$MTAC_{glc}$, $MTAC_{un}$ and $MTAC_c$ for each solute and $_rL_PS_C$, in reality, tend to vary largely according to peritoneal function of individual patients, and they individually take values specific to each patient. Taking this point into account, the second embodiment explicitly treats these four parameters as dynamic variables, and enables more precise and accurate dialysis planning to be performed according to peritoneal function of individual patients.

Note that multi-dimensional equations need to be solved here since the above new parameter is added, which leads to an increase in the computational freedom. As a result, the peritoneal function testing program of the first embodiment with no modification cannot cover the increased freedom of computation. To reduce the computational burden, in the peritoneal function testing program of the second embodiment, computation of the Three-Pore Theory formulae in combination with the Genetic Algorithm is carried out on the results obtained by calculating the Pyle-Popovich model, which facilitates to narrow the parameter values to the optimal solution. Since the Genetic Algorithm is a technique for converging the computation outcome to the optimal solution, with the use of evaluation functions, by repeating a specific amount of computation for provided initial estimate values, the use of the Genetic Algorithm enables rather quick computation.

2.2 Configuration and Operations of Peritoneal Function Testing Program

The peritoneal function testing program of the second embodiment is configured to be generally executed in the following sequence. Here is described the program configuration together with a practical example including how to collect clinical data.

Figure 13:
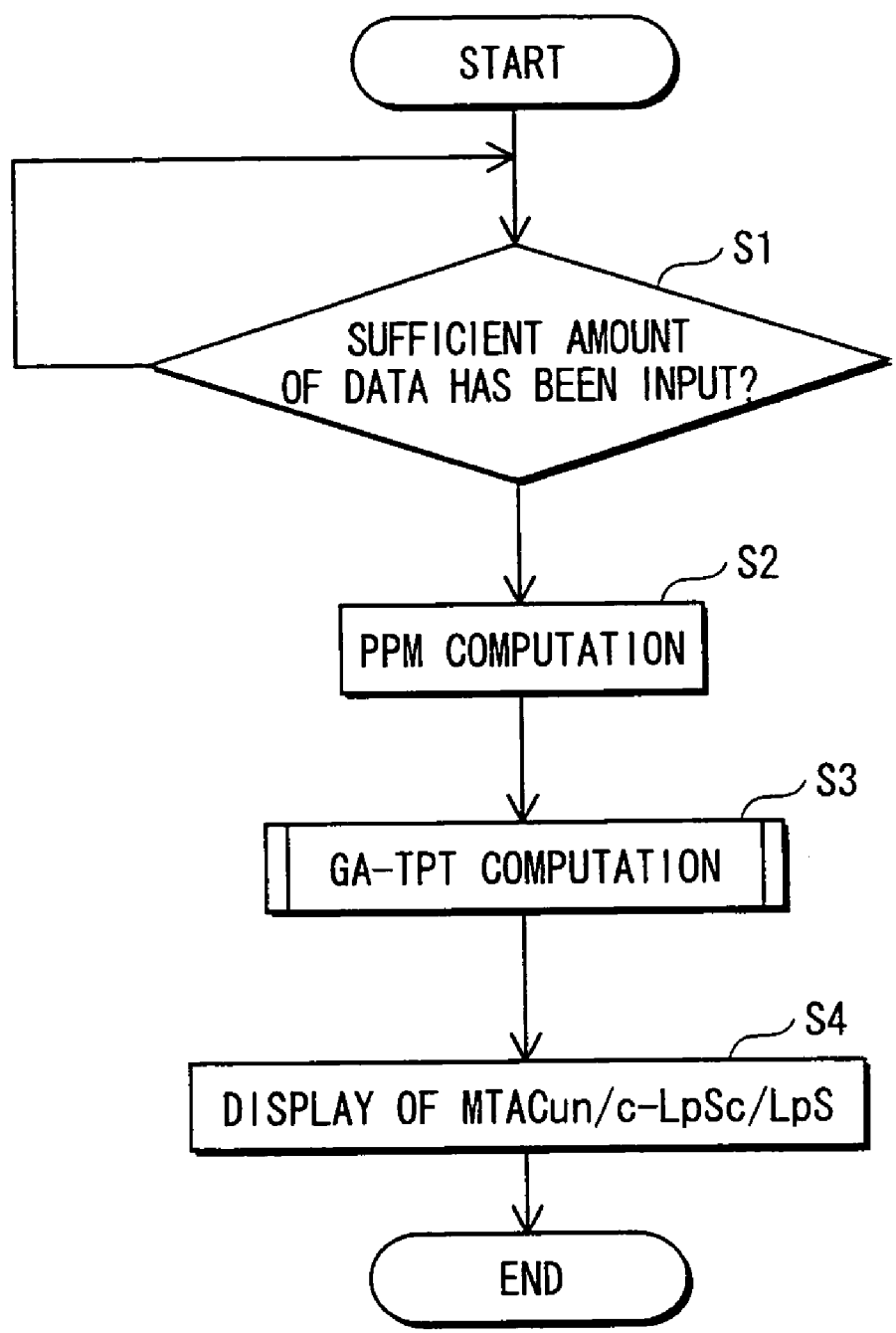
FIG. 13 is a flowchart of exemplified steps of a program, from data input to display of peritoneal function.

FIG. 13 is a flow diagram showing exemplified steps of the peritoneal function testing program, from data input to display of peritoneal function. "PPM" in the figure means the Pyle-Popovich model while "TPT" denotes the Three-Pore Theory. A main characteristic of this process flow is a GA-TPT computation step (Step S3).

According to the process flow shown in FIG. 13, when the program is executed, the operator inputs patient's clinical data required for the peritoneal function test to the PC 1 of the peritoneal dialysis planning apparatus. The data items are as shown in charts of FIGS. 6 and 7. However, in the second embodiment, only the amount of total protein may be measured while the measurement of albumin in drained fluid being omitted. This is because the concentration of albumin in drained fluid is proportional to the concentration of total protein. Alternatively, it is possible to obtain the amount of albumin from the amount of total protein.

Figure 15:
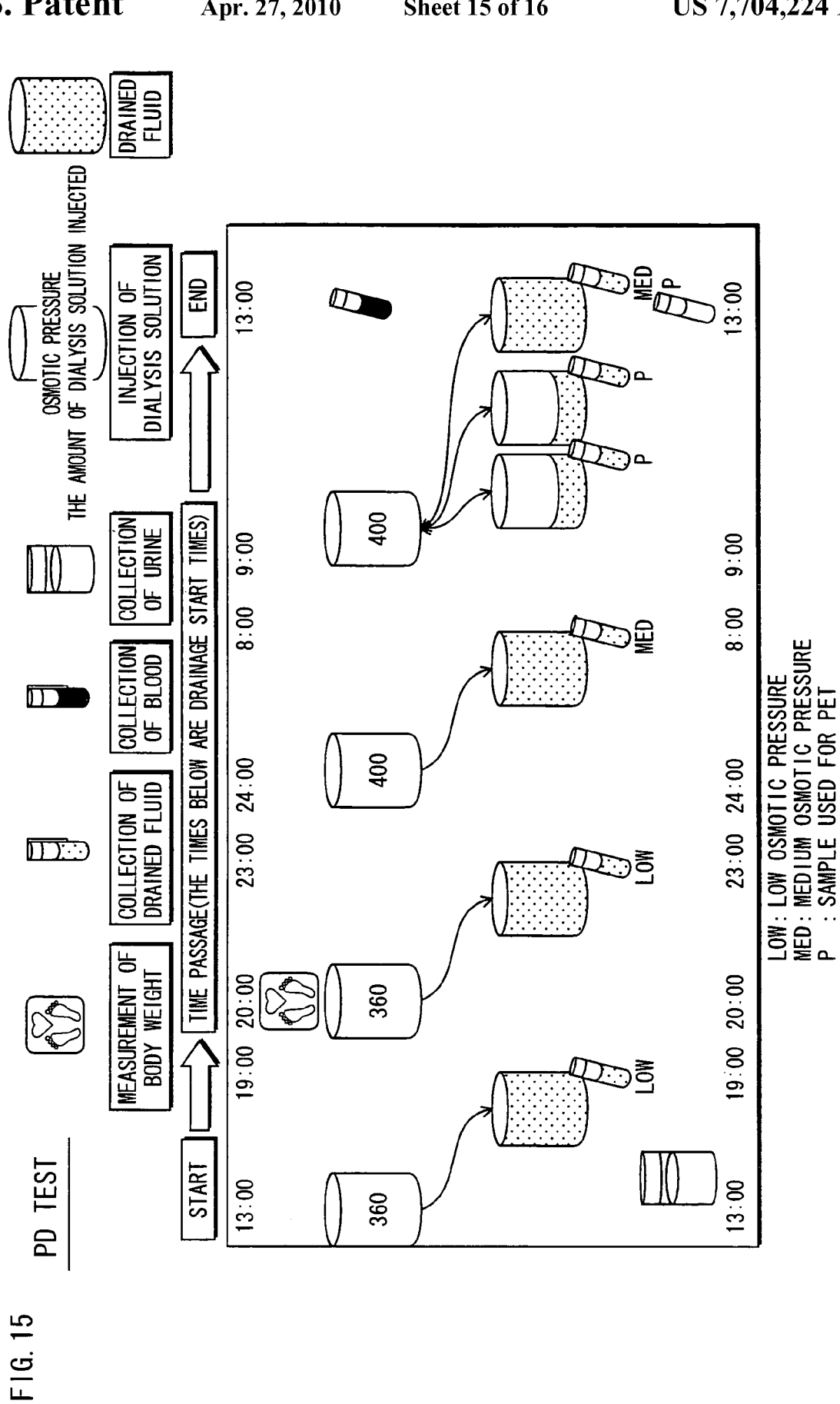
FIG. 15 shows an example of a time chart of a peritoneal test.

A schedule (time chart) for collecting necessary clinical data is characterized by starting, for example, at 1 o'clock in the afternoon on the previous day of a hospital visit, with acquisition of data on the amount of drained fluid and the amount of collected urine performed by a patient himself, and finished with one-time-only blood sample collection carried out when the patient visits the hospital on the next day (1:00 p.m.), as shown in FIG. 15.

In the second embodiment, the required clinical data is reduced to the amount that can be collected in one hospital visit of a patient—to be specific, the number of clinical data sets is reduced to four (i.e. the number of dialysis solution exchanges) and the blood sampling is limited to once, as shown in a comparative diagram of FIG. 16. The clinical data collection at hospital can be carried out together with a regular medical checkup, and thus the second embodiment can reduce not only patient's burden and labor but also the workload of staff collecting clinical data, as compared to the first embodiment. This is because only a smaller number of data sets are required for computation thanks to the adoption of the Genetic Algorithm to the program, which is described hereinafter.

When the input of the above data is complete, the peritoneal function testing program becomes executable. Then, if the amount of the input data is sufficient in just proportion (Step S1), the program carries out a first computational step—computation of the Pyle-Popovich model—according to the operator's direction (Step S2).

Here, the computation of the Pyle-Popovich model is basically executed in the same process as in the first embodiment. However, in the second embodiment, the formula (1-2) of the mathematical expression I is simplified.

Namely, it is here assumed that the blood concentration of solutes during the dialysis is fairly constant, and therefore an approximate constant is assigned to $C_B$ in the formula (1-2). Herewith, only $C_D$ is virtually a variable in the formula (1-2), which simplifies the formula to be a linear differential equation. Such simplification of making the formula (1-2) be a linear differential equation is justified based on the judgment that assigning an approximate value to $C_B$ at this point has no significant effect on the final result in the case where the computed results of the Pyle-Popovich model are treated as initial estimate values for the calculation of the Three-Pore Theory formulae.

Note that simplifying the formula (1-2) to a linear differential equation is not indispensable for the present invention. However, without the simplification, the same number of clinical data sets is required as in the first embodiment.

From the results of the Pyle-Popovich model obtained in this way, the respective parameter values including $MTAC_{glc}$, $MTAC_{un}$, $MTAC_c$, $\sigma$, $a_1$, $a_2$, $a_3$ and $_rL_PS_C$ are, as in the first embodiment, calculated. Of them, the values of $MTAC_{glc}$, $MTAC_{un}$, $MTAC_c$ and $_rL_PS_C$ are used as an unknown parameter set (initial estimate values) for the computation of the Three-Pore Theory.

After obtaining values of the individual parameters above, computation of the Genetic Algorithm and the Three-Pore Theory (GA-TPT computation) is carried out as a second computational step, which is a characteristic of the present embodiment (Step S3). Here, an elite parameter set (an optimal solution) is obtained from the unknown parameter set (initial estimate values) through the computation of the Genetic Algorithm, and then the formulae of the Three-Pore Theory are solved using the elite parameter set.

Figure 14:
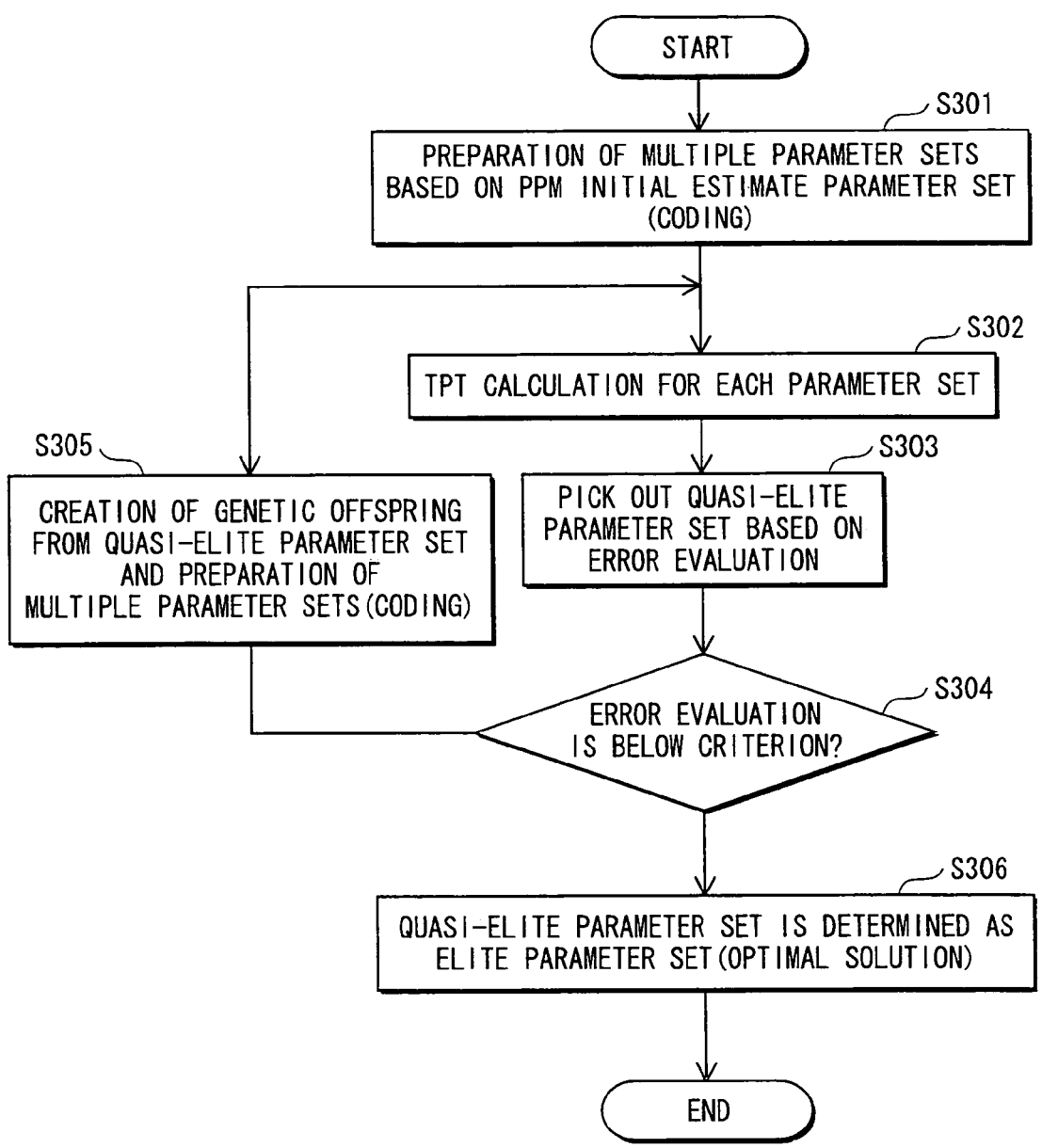
FIG. 14 is a flowchart illustrating a specific computational process of a Genetic Algorithm and the Three-Pore Theory.

FIG. 14 is a flowchart specifically illustrating a process of the computation of the Genetic Algorithm and the Three-Pore Theory (GA-TPT computation) in Step S3.

As shown in the figure, in Step S3, the PC 1 prepares multiple parameter sets through coding operations using the Genetic Algorithm, based on the parameter set (the initial estimate parameter set) which comprises four unknown parameters obtained from the Pyle-Popovich model above (Step S301). Here, the initial estimate parameter set itself may be included in the prepared multiple parameter sets.

Next, the PC 1 computes the Three-Pore Theory by using each of the multiple parameter sets (Step S302). The computation of the Three-Pore Theory is carried out in the same manner as in the first embodiment, using the mathematical expressions II to V. Then, the PC 1 performs error evaluation for the computational result of each parameter set. For the error evaluation, an error calculation method is employed in which the following formulae (7-1) and (7-2) of the mathematical expression VII are used as evaluation functions, and an estimated amount of drained fluid $V_{DEST}$ and an estimated concentration of solution in the drained fluid $C_{DsEST}$ are respectively checked against actual measurements ($V_{DCLN}$, $C_{DsCLN}$).

[Mathematical Expression VII]

$$Err_{VD} = \sum \frac{(V_{DEST} - V_{DCLN})^2}{V_D(0)} \qquad (7\text{-}1)$$

$$Err_{CDs} = \sum \frac{(C_{DsEST} - C_{DsCLN})^2}{C_{Ds}(0)} \quad (7\text{-}2)$$

Subsequently, the PC 1 selects and leaves a parameter set with the smallest error obtained in the error evaluation of Step S302 (Step S303). The parameter set selected here is called, for example, a "quasi-elite parameter set".

Then, the PC 1 judges whether or not the error of the quasi-elite parameter set is less than a reference value (Step S304).

As one example of the reference value for the judgment in Step S304, the second embodiment requires the error of the mathematical expression VII to be less than 5%. If the error between $V_{DEST}$ and $C_{DsEST}$ of the quasi-elite parameter set and the actual measurements $V_{DCLN}$ and $C_{DsCLN}$ is as large as to be greater than or equal to the reference value—namely, 5% or more, a value of each parameter in the current quasi-elite parameter set is crossed based on the Genetic Algorithm to create genetic offspring, while coding operations being performed to thereby prepare newly created multiple parameter sets (Step S305).

The operation procedure of the crossing includes, for example, changing each parameter value of the quasi-elite parameter set from a decimal number to a binary-coded form and making high-order and lower-order bits in each value shuffled. Note that the present invention may use a shuffling technique other than this—for example, empirically narrowing down the range of a value by using the normal distribution which indicates the existing probability of the parameter. Or alternatively, the parameter value and the error may be respectively plotted on each of crossed axes so as to create a landscape (map), and the range of the value can be narrowed down, around local minimum points shown on the map.

Then, steps of S302, S303, S304 and S05 are repeated in the stated order until the computed values of the Three-Pore Theory and the actual measurements have better fitness with the error between them reaching less than 5% in Step S304.

If the error is judged to be less than 5% in Step S304, the quasi-elite parameter set at this point is determined as an elite parameter set (an optimal solution) (Step S306), and then the process flow of the GA-PTP computation is brought to completion.

As shown in Step S4 of FIG. 13, the PC 1 subsequently outputs, to the display 10, either one of correlation diagrams pertaining to $MTAC_{un}/_c$ v.s. the volume of water removal or $MTA_{Cun}/_c$ v.s. $L_PS_C/L_PS$ (the same as FIGS. 9 to 12), which are created based on the results obtained from the Three-Pore Theory computation using the elite parameter set and the earlier computed results from the Pyle-Popovich model.

Thus, in the second embodiment, the initial estimate parameter set obtained from the Pyle-Popovich model is fitted according to an individual patient, then the computation of the Three-Pore Theory is carried out based on the fitted initial estimate parameter set, and the computed results are presented on a display. Therefore, the second embodiment is capable of performing accurate and detailed dialysis planning which is further more specific to individual patients. In addition, work required of patients and data examiners to implement the second embodiment can be reduced, which in turn leads to alleviating their mental burden and letting them take a relaxed attitude toward the testing. As a result, dialysis planning may be reviewed once and again, and it is also expected to bring an effect that the best-suited dialysis plan is offered to patients each time.

It is a matter of course that the error reference in Step S304 of the above process flow can take a value other than 5%. As a rough guide for setting the reference value, it is desirable to refer to data on daily prescription (data on drained fluid, etc.) tailored to individual patients.

In addition, multiple quasi-elite parameter sets may be selected in Step S303. In this case, only one elite parameter set will be selected from the multiple quasi-elite parameter sets. When the error reaches or exceeds the reference value, crossing is performed within the multiple quasi-elite parameter sets to calculate the genetic offspring.

3. Additional Particulars

The present invention provides an example of deriving $L_PS_C/L_PS$ by using data obtained from the Three-Pore Theory model and using this ratio as an index of the peritoneal function test. Instead of the water permeability coefficient of aquaporins $L_PS_C$, however, the water permeability coefficients of pores transferring medium- and small-sized molecules $L_PS_L$ and $L_PS_S$ may be used to calculate a ratio to $L_PS$ since similar proportional relations can theoretically be observed. Practically speaking, however, pores transferring medium- and small-sized molecules have variations in the rate of transferring solutes, and problems of reproducibility are not negligible. Therefore, the use of these water permeability coefficients $L_PS_L$ and $L_PS_S$ is less recommended.

Although the first embodiment shows an example of computing the Pyle-Popovich model and the Three-Pore Theory model by using data obtained from a patient and calculating $MTAC_{un}/_c$ and $L_PS_C/L_PS$, the present invention is not limited to this. Each value of $MTAC_{un}$, $MTAC_c$, $L_PS_C$, $L_PS$ and the like already obtained by a computing unit of a different apparatus may be used as input data, and $MTAC_{un}/_c$ and $L_PS_C/L_PS$ may be calculated from the input data, for example.

In addition, $MTAC_{un}$ and $MTAC_c$ can be derived from a mathematical model other than the Pyle-Popovich model.

Furthermore, in the above embodiments, the display 10 is used as an example of data output means. However, the present invention is not confined to this, and data may be output by audio using speakers.

The present invention is applicable to the study of peritoneal dialysis planning in dialysis treatment.

The invention claimed is:

1. A peritoneal function testing method comprising:
providing a computation unit;
obtaining data of a dialysis patient using the computation unit;
a 1st computation step of obtaining individual initial estimate values for (i) $MTAC_{glc}$, $MTAC_{un}$, and $MTAC_c$ by using the obtained data and a processor of the computation unit to compute a Pyle-Popovich model, and (ii) a $L_PS_C/L_PS$ ratio by using $L_PS_C$ and $L_PS$, where $MTAC_{glc}$ is an overall mass transfer-area coefficient for glucose, $MTAC_{un}$ is an overall mass transfer-area coefficient for urea nitrogen, $MTAC_c$ is an overall mass transfer-area coefficient for creatinine, $L_PS_C$ is a permeability coefficient for cell pores, and $L_PS$ is an overall permeability coefficient;
a 2nd computation step, following the 1st computation step, of using the computation unit to (i) obtain computation results by computing a Three-Pore Theory model using the individual initial estimate values for the $MTAC_{glc}$, the $MTAC_{un}$, the $MTAC_c$, and the $L_PS_C/L_PS$ ratio obtained by the 1st computation step, and (ii) calculate an optimal solution of the computation results obtained by computing the Three-Pore Theory model, the optimal solution being calculated using a Genetic Algorithm; and using a $MTAC_{un}/MTAC_c$ ratio, which is calculated using an optimal $MTAC_{un}$ and an optimal $MTAC_c$ determined using the optimal solution, as an index for a peritoneal function test.

2. The peritoneal function testing method of claim 1, wherein in the 1st computation step including the computing of the Pyle-Popovich model, solute concentration values for the glucose, the urea nitrogen, and the creatinine are individually calculated as approximation solutions of linear differential equations.

3. The peritoneal function testing method of claim 2, wherein the $MTAC_{un}/MTAC_c$ ratio and a volume of water removal are used as indexes for the peritoneal function test.

4. The peritoneal function testing method of claim 3, wherein a correlation between the $MTAC_{un}/MTAC_c$ ratio and the volume of water removal is used as an index for the peritoneal function test.

5. A peritoneal dialysis planning apparatus comprising:
a processor;
a memory;
a computation unit programmed to (i) obtain data of a dialysis patient and store the obtained data in the memory, (ii) obtain individual initial estimate values for $MTAC_{glc}$, $MTAC_{un}$, and $MTAC_c$ by using the obtained data and the processor to compute a Pyle-Popovich model and for a $L_P S_C/L_P S$ ratio by using $L_P S_C$ and $L_P S$, where $MTAC_{glc}$ is an overall mass transfer-area coefficient for glucose, $MTAC_{un}$ is an overall mass transfer-area coefficient for urea nitrogen, $MTAC_c$ is an overall mass transfer-area coefficient for creatinine, $L_P S_C$ is a permeability coefficient for cell pores, and $L_P S$ is an overall permeability coefficient, (iii) obtain computation results by computing a Three-Pore Theory model using the processor and the individual initial estimate values for the $MTAC_{glc}$, the $MTAC_{un}$, the $MTAC_c$, and the $L_P S_C/L_P S$ ratio, (iv) calculate, using the processor and a Genetic Algorithm, an optimal solution of the computation results obtained by computing the Three-Pore Theory model, and (v) calculate a $MTAC_{un}/MTAC_c$ ratio using the processor, an optimal $MTAC_{un}$ determined using the optimal solution and an optimal $MTAC_c$ determined using the optimal solution; and
an output unit operable to output the $MTAC_{un}/MTAC_c$ ratio as an index for a peritoneal function test.

6. The peritoneal dialysis planning apparatus of claim 5, wherein during the computation of the Pyle-Popovich model, the computation unit calculates individual solute concentration values for the glucose, the urea nitrogen, and the creatinine, as approximation solutions of linear differential equations.

7. The peritoneal dialysis planning apparatus of claim 5, wherein a correlation between (i) the $MTAC_{un}/MTAC_c$ ratio calculated using the optimal $MTAC_{un}$ and the optimal $MTAC_c$ and (ii) a volume of water removal, is presented in a graph that is output to the output unit.

8. The peritoneal dialysis planning apparatus of claim 7, wherein the output unit is a display unit, and
wherein the display unit outputs the correlation by displaying a distribution of plotted actual measurements of multiple patients and a regression line for the distribution.

9. The peritoneal dialysis planning apparatus of claim 5, wherein the output unit outputs one of the $MTAC_{un}/MTAC_c$ ratio calculated using the optimal solution and the $L_P S_C/L_P S$ ratio calculated using the optimal solution, which is plotted in a two axis coordinate system together with a volume of water removal.

10. A computer-readable recording medium having a peritoneal function testing program recorded thereon, the peritoneal function testing program causing a computer to execute a peritoneal function testing method comprising:
a 1st computation step of obtaining data of a dialysis patient using a computation unit and obtaining individual initial estimate values for (i) $MTAC_{glc}$, $MTAC_{un}$, and $MTAC_c$ by using the obtained data and a processor of the computation unit to compute a Pyle-Popovich model, and (ii) a $L_P S_C/L_P S$ ratio by using $L_P S_C$ and $L_P S$, where $MTAC_{glc}$ is an overall mass transfer-area coefficient for glucose, $MTAC_{un}$ is an overall mass transfer-area coefficient for urea nitrogen, $MTAC_c$ is an overall mass transfer-area coefficient for creatinine, $L_P S_C$ is a permeability coefficient for cell pores, and $L_P S$ is an overall permeability coefficient;
a 2nd computation step, following the 1st computation step, of using the computation unit to (i) obtain computation results by computing a Three-Pore Theory model using the individual initial estimate values for the $MTAC_{glc}$, the $MTAC_{un}$, the $MTAC_c$, and the $L_P S_C/L_P S$ ratio obtained by the 1st computation step, and (ii) calculate an optimal solution of the computation results obtained by computing the Three-Pore Theory model, the optimal solution being calculated using a Genetic Algorithm; and
using a $MTAC_{un}/MTAC_c$ ratio, which is calculated using an optimal $MTAC_{un}$ and an optimal $MTAC_c$ determined using the optimal solution, as an index for a peritoneal function test.

11. The computer-readable recording medium of claim 10, wherein the peritoneal function testing method includes, during the 1st computation step including the computing of the Pyle-Popovich model, calculating individual solute concentration values for the glucose, the urea nitrogen, and the creatinine, as approximation solutions of linear differential equations.

12. The computer-readable recording medium of claim 10, wherein the peritoneal function testing method includes using the $MTAC_{un}/MTAC_c$ ratio and a volume of water removal as indexes for the peritoneal function test.

* * * * *